United States Patent [19]

Van Lommen et al.

[11] Patent Number: 5,824,682

[45] Date of Patent: Oct. 20, 1998

[54] VASOCONSTRICTIVE DIHYDROBENZOPYRAN DERIVATIVES

[75] Inventors: Guy Rosalia Eugène Van Lommen, Berlaar; Piet Tom Bert Paul Wigerinck, Turnhout; Marcel Frans Leopold De Bruyn, Wortel; Wim Gaston Verschueren, Berchem; Marc Francis Josephine Schroven, Wiekevorst, all of Belgium

[73] Assignee: Janssen Pharmaceutica, N.V., Beerse, Belgium

[21] Appl. No.: 586,760

[22] PCT Filed: Aug. 12, 1994

[86] PCT No.: PCT/EP94/02703

§ 371 Date: Jan. 30, 1996

§ 102(e) Date: Jan. 30, 1996

[87] PCT Pub. No.: WO95/05383

PCT Pub. Date: Feb. 23, 1995

[30] Foreign Application Priority Data

| Aug. 18, 1993 | [EP] | European Pat. Off. | 93202441 |
| Aug. 18, 1993 | [EP] | European Pat. Off. | 93202442 |
| Aug. 18, 1993 | [EP] | European Pat. Off. | 93202443 |

[51] Int. Cl.⁶ .................. A61K 31/35; C07D 493/04; C07D 405/12; C07D 311/58

[52] U.S. Cl. .................. 514/256; 514/247; 514/255; 544/180; 544/224; 544/242; 544/336; 546/282.1

[58] Field of Search .................. 514/373, 247, 514/255, 256; 544/322, 180, 242, 366, 224; 546/282.1

[56] References Cited

U.S. PATENT DOCUMENTS

| 4,405,622 | 9/1983 | Kluge .................. 544/295 |
| 5,137,901 | 8/1992 | Junge et al. .................. 514/373 |
| 5,541,180 | 7/1996 | Van Lommen et al. |

FOREIGN PATENT DOCUMENTS

| 0 352 613 | 1/1990 | European Pat. Off. .................. 417/12 |
| WO A 93/17017 | 9/1993 | WIPO .................. 405/12 |

Primary Examiner—Mukund J. Shah
Assistant Examiner—Pavanaram K. Sripada

[57] ABSTRACT

The present invention is concerned with compounds of formula

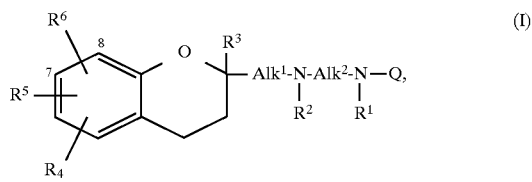

the pharmaceutically acceptable acid addition salts thereof, and the stereochemically isomeric forms thereof, wherein $R^1$ is hydrogen or $C_{1-6}$alkyl; $R^2$ is hydrogen or $C_{1-6}$alkyl; $R^3$ is hydrogen or $C_{1-6}$alkyl; $R^4$ is hydrogen, halo, $C_{1-6}$alkyl, hydroxy, $C_{1-6}$alkyloxy, aryloxy or arylmethoxy; $R^5$ and $R^6$ designate $R^{5a}$ and $R^{6a}$ wherein $R^{5a}$ and $R^{6a}$ taken together form a bivalent radical; or $R^5$ and $R^6$ can designate $R^{5b}$ and $R^{6b}$ wherein $R^{5b}$ is hydrogen and $R^{6b}$ is a heterocycle or an optionally substituted alkenyl or alkynyl group; or $R^5$ and $R^6$ designate $R^{5c}$ and $R^{6c}$, wherein $R^{5c}$ and $R^{6c}$ are hydrogen, halo, $C_{1-6}$alkyl, $C_{3-6}$alkenyl, $C_{3-6}$alkynyl, hydroxy, $C_{1-6}$alkyloxy, cyano, amino$C_{1-6}$alkyl, carboxyl, $C_{1-6}$alkyloxycarbonyl, nitro, amino, aminocarbonyl, $C_{1-6}$alkylcarbonylamino, or mono-di($C_{1-6}$alkyl)amino; Q is a heterocyclic ring containing at least one nitrogen atom or a radical of formula

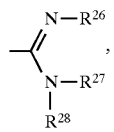

pharmaceutical compositions, preparations and use as a medicine are also described.

7 Claims, No Drawings

VASOCONSTRICTIVE DIHYDROBENZOPYRAN DERIVATIVES

CROSS-REFERENCE TO RELATED APPLICATIONS

This application is based upon PCT Application Ser. No. PCT/EP 94/02703, filed Aug. 12, 1994, which claims priority from European Patent Application Ser. No. 93.202.443.3, filed on Aug. 19, 1993; European Patent Application Ser. No. 93.202.442.5, filed on Aug. 19, 1993; and European Patent Application Ser. No. 93.202.441.7, filed on Aug. 19, 1993.

The present invention relates to novel dihydrobenzopyran derivatives, processes for their preparations, pharmaceutical compositions containing them and their use as a medicine, in particular for the prevention and/or treatment of disorders characterized by excessive vasodilatation, especially migraine.

Migraine is a non-lethal disease suffered by one in ten individuals. The main symptom is headache; other symptoms include vomiting and photophobia. For many years the most widely used treatment for migraine involved the administration of ergotalkaloids, which show however several adverse side effects. Recently a tryptamine derivative, i.e. sumatriptan, was introduced as a novel antimigraine drug. We have now surprisingly found that the present novel dihydrobenzopyran derivatives show 5-HT$_1$-like agonistic activity and can thus be used in the treatment of disorders characterized by excessive vasodilatation, especially migraine.

The present invention is concerned with compounds of formula

![Formula I structure: dihydrobenzopyran with R$^6$, R$^5$, R$^4$ substituents on aromatic ring (positions 7, 8), R$^3$ on pyran, and -Alk$^1$-N(R$^2$)-Alk$^2$-N(R$^1$)-Q chain] (I)

the pharmaceutically acceptable acid or base addition salts thereof, and the stereochemically isomeric forms thereof, wherein R$^1$, R$^2$ and R$^3$ each independently are hydrogen or C$_{1-6}$alkyl;

R$^4$ is hydrogen, halo, C$_{1-6}$alkyl, hydroxy, C$_{1-6}$alkyloxy, aryloxy or arylmethoxy;

R$^5$ and R$^6$ designate R$^{5a}$ and R$^{6a}$,
  wherein R$^{5a}$ and R$^{6a}$ are taken together to form a bivalent radical, which is linked to the 7 and 8 position of the dihydrobenzopyran moiety, and has the formula

| | |
|---|---|
| —CH=CH—CH=CH— | (a1), |
| —(CH$_2$)$_n$— | (a2), |
| —(CH$_2$)$_m$—X— | (a3), |
| —X—(CH$_2$)$_m$— | (a4), |
| —CH=CH—X— | (a5), |
| —X—CH=CH— | (a6), |
| —O—(CH$_2$)$_t$—Y— | (a7), |
| —Y—(CH$_2$)$_t$—O— | (a8), |
| —(CH$_2$)$_t$—Z— | (a9), |
| —Z—(CH$_2$)$_t$— | (a10), |
| —CH=CH—Z— | (a11), |
| —Z—CH=CH— | (a12), |
| —NH—C(A)=N— | (a13), |
| —O—C(A)=N— | (a14), |
| —N=C(A)—O— | (a15); | in these bivalent radicals one or two hydrogen atoms may be substituted with

C$_{1-6}$alkyl, C$_{1-6}$alkylcarbonyl or C$_{1-6}$alkyl-S(O)—;

n is 3 or 4;

each X independently is —O—, —S—, —S(O)—, —(O)$_2$—, —C(O)—, —NR$^7$—;

each m independently is 2 or 3;

each Y independently is —O—, —S—, —S(O)—, —(O)$_2$—, —C(O)—, —NR$^7$—;

Z is —O—C(O)—, —C(O)—O—, —NH—C(O)—, —C(O)—NH—;

each t independently is 1 or 2;

R$^7$ is hydrogen, C$_{1-6}$alkyl, C$_{1-6}$alkylcarbonyl or C$_{1-6}$alkyl-S(O)—, each A independently is hydroxy, C$_{1-6}$alkyl, C$_{1-6}$alkyloxy;

or R$^5$ and R$^6$ designate R$^{5b}$ and R$^{6b}$, wherein R$^{5b}$ is hydrogen and R$^{6b}$ is hydroxyC$_{1-6}$alkyl, carboxyl C$_{1-6}$alkyl, C$_{1-6}$alkyloxycarbonylC$_{1-6}$alkyl, trihalomethyl, C$_{1-6}$alkylcarbonyl, C$_{1-6}$alkyloxycarbonylC$_{1-6}$alkyl-S—, carboxyl C$_{1-6}$alkyl-S—, C$_{1-6}$alkyl-S—, C$_{1-6}$alkyl-S(O)—, aryl-S—, aryl-S(O)— or R$^{6b}$ is a radical of formula $-C\equiv C-R^8$, (b1)

$-CH=CH-R^9$, (b2)

![phenyl with R$^{10}$, R$^{11}$] (b3)

![pyridinyl with R$^{12}$, R$^{13}$] (b4)

![furan with R$^{14}$, R$^{15}$] (b5)

![thiophene with R$^{16}$, R$^{17}$] (b6)

![imidazole with R$^{18}$, R$^{19}$] (b7)

![oxazole with R$^{20}$] (b8)

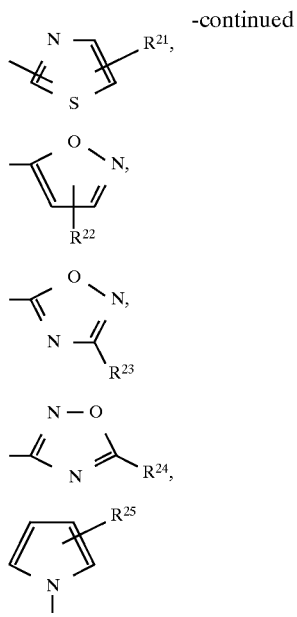

(b9)

(b10)

(b11)

(b12)

(b13)

R⁸ and R⁹ each independently are hydrogen, carboxyl, $C_{1-6}$alkyloxycarbonyl, aminocarbonyl, mono- or di($C_{1-6}$alkyl)aminocarbonyl;

$R^{10}$, $R^{11}$, $R^{12}$, $R^{13}$, $R^{14}$, $R^{15}$, $R^{16}$ and $R^{17}$ each independently are hydrogen, halo or $C_{1-6}$alkyl;

$R^{18}$, $R^{19}$, $R^{20}$, $R^{21}$, $R^{22}$, $R^{23}$, $R^{24}$ and $R^{25}$ each independently are hydrogen or $C_{1-6}$alkyl;

or $R^5$ and $R^6$ designate $R^{5c}$ and $R^{6c}$ in which case $R^4$ can only mean hydrogen; and $R^{5c}$ and $R^{6c}$ each independently are hydrogen, halo, $C_{1-6}$alkyl, $C_{3-6}$alkenyl, $C_{3-6}$alkynyl, hydroxy, $C_{1-6}$alkyloxy, cyano, amino $C_{1-6}$alkyl, carboxyl, $C_{1-6}$alkyloxycarbonyl, nitro, amino, aminocarbonyl, $C_{1-6}$alkylcarbonylamino, or mono- or di($C_{1-6}$alkyl)amino;

Alk¹ is $C_{1-5}$alkanediyl;

Alk² is $C_{2-15}$alkanediyl;

Q is a radical of formula

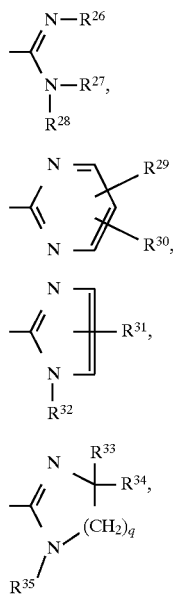

(aa)

(bb)

(cc)

(dd)

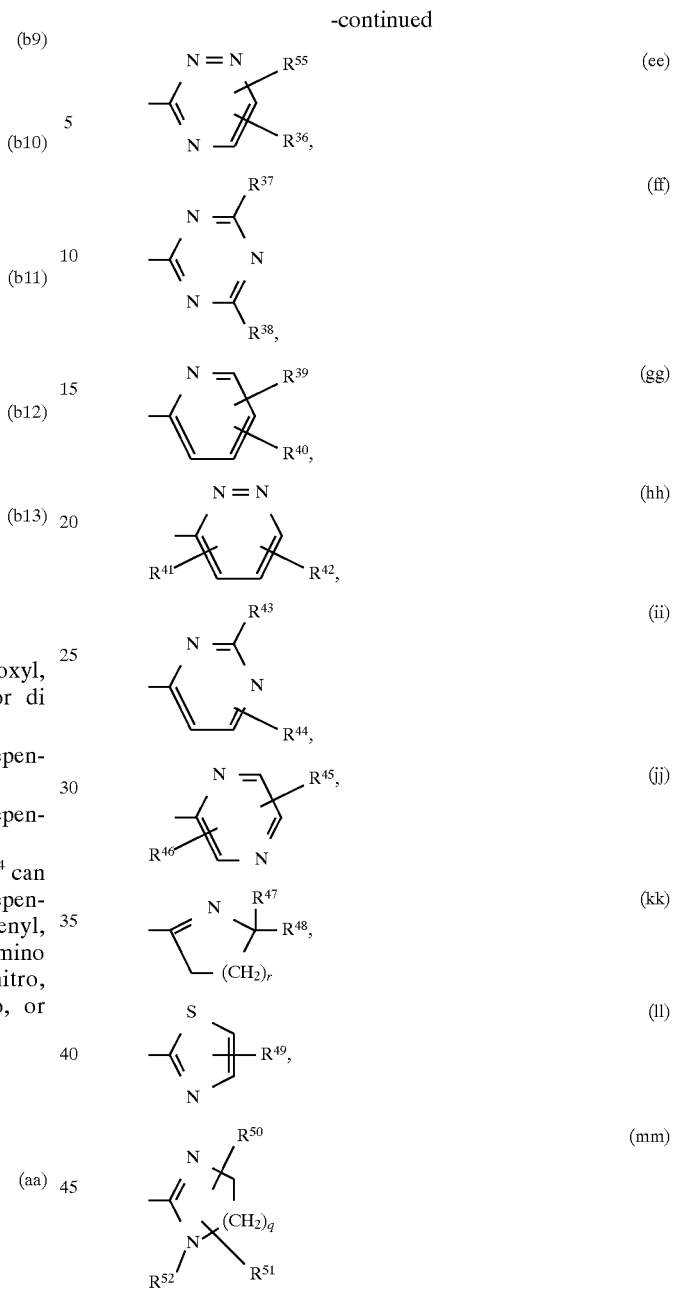

wherein
  $R^{26}$ is hydrogen, cyano, aminocarbonyl or $C_{1-6}$alkyl;
  $R^{27}$ is hydrogen, $C_{1-6}$alkyl, $C_{3-6}$alkenyl, $C_{3-6}$alkynyl, $C_{3-6}$cycloalkyl or aryl$C_{1-6}$alkyl
  $R^{28}$ is hydrogen or $C_{1-6}$alkyl; or
  $R^{27}$ and $R^{28}$ taken together form a bivalent radical of formula —(CH₂)₄—, —(CH₂)₅—, or a piperazine which is optionally substituted with $C_{1-6}$alkyl;
  $R^{29}$, $R^{30}$, $R^{31}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{53}$, $R^{54}$ and $R^{55}$ each independently are hydrogen, hydroxy, halo, $C_{1-6}$alkyl, $C_{1-6}$alkyloxy, aryloxy, aryl$C_{1-6}$alkyl, $C_{1-6}$alkylthio, cyano, amino, mono- or di($C_{1-6}$alkyl)

amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;

$R^{32}$, $R^{35}$ and $R^{52}$ each independently are hydrogen, $C_{1-6}$alkyl, $C_{1-6}$alkylcarbonyl, or aryl$C_{1-6}$alkyl;

q is 1, 2 or 3;

$R^{33}$ and $R^{34}$ are each hydrogen or taken together with the carbon atom to which they are connected they can form C(O);

r is 1, 2 or 3;

$R^{47}$ and $R^{48}$ are each hydrogen or taken together with the carbon atom to which they are connected they can form C(O);

$R^{49}$ is hydrogen, halo or $C_{1-6}$alkyl;

$R^{50}$ is hydrogen and $R^{51}$ is hydroxy; or $R^{50}$ and $R^{51}$ taken together may form a bivalent radical of formula $(CH_2)_3$ or $(CH_2)_4$ which is optionally substituted with $C_{1-6}$alkyl;

aryl is phenyl optionally substituted with hydroxy, halo, $C_{1-6}$alkyl, $C_{1-6}$alkyloxy;

with the proviso that when $R^4$ is hydrogen and $R^5$ and $R^6$ designate $R^{5c}$ and $R^{6c}$ then Q must be a radical of formula (gg); (hh); (ii); (jj); (kk); (ll); (mm); (nn); a radical of formula (aa) wherein $R^{27}$ is $C_{3-6}$cycloalkyl or aryl$C_{1-6}$alkyl; a radical of formula (aa) wherein $R^{27}$ and $R^{28}$ taken together with the nitrogen atom to which they are attached form a piperazine which is optionally substituted with $C_{1-6}$alkyl; a radical of formula (bb) wherein $R^{29}$ is hydroxy on a carbon atom adjacent to a nitrogen atom; a radical of formula (dd) wherein $R^{35}$ is hydrogen and $R^{33}$ and $R^{34}$ taken together with the carbon atom to which they are attached form C(O); a radical of formula (ee) wherein $R^{55}$ is aryl$C_{1-6}$alkyl.

Some of the compounds of formula (I) may also exist in their tautomeric forms. Such forms although not explicitly indicated in the above formula are intended to be included within the scope of the present invention.

As used in the foregoing definitions and hereinafter halo defines fluoro, chloro, bromo and iodo; $C_{1-6}$alkyl defines straight and branch chained saturated hydrocarbon radicals having from 1 to 6 carbon atoms such as, for example, methyl, ethyl, propyl, butyl, pentyl, hexyl and the like; $C_{3-6}$alkenyl defines straight and branch chained hydrocarbon radicals containing one double bond and having from 3 to 6 carbon atoms, such as, for example, 2-propenyl, 3-butenyl, 2-butenyl, 2-pentenyl, 3-pentenyl, 3-methyl-2-butenyl and the like; and the carbon atom of said $C_{3-6}$alkenyl being connected to a nitrogen atom preferably is saturated, $C_{3-6}$alkynyl defines straight and branch chained hydrocarbon radicals containing one triple bond and having from 3 to 6 carbon atoms, such as, for example, 2-propynyl, 3-butynyl, 2-butynyl, 2-pentynyl, 3-pentynyl, 3-hexynyl, and the like; and the carbon atom of said $C_{3-6}$alkynylradical being connected to a nitrogen atom preferably is saturated; $C_{3-6}$cycloalkyl is generic to cyclopropyl, cyclobutyl, cyclopentyl and cyclohexyl; $C_{1-5}$alkanediyl defines bivalent straight and branch chained saturated hydrocarbon radicals having form 1 to 5 carbon atoms, such as, for example, methylene, 1,2-ethanediyl, 1,3-propanediyl, 1,4-butanediyl or 1,5-pentanediyl and the branched isomers thereof; $C_{2-15}$alkanediyl defines bivalent straight and branch chained saturated hydrocarbon radicals having from 2 to 15 carbon atoms such as, for example, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl, 1,13-tridecanediyl, 1,14-tetradecanediyl, 1,15-pentadecanediyl, and the branched isomers thereof. The terms $C_{1-4}$alkanediyl, $C_{2-6}$alkanediyl and $C_{2-14}$alkanediyl are defined in an analogous manner. The term "C(O)" refers to a carbonyl group.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may also be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic saturated hydrocarbon radicals may have either the cis- or trans-configuration and $C_{3-6}$-alkenyl radicals may have the E- or Z-configuration. Stereochemically isomeric forms of the compounds of formula (I) are obviously intended to be embraced within the scope of this invention.

$R^1$ is suitably methyl or hydrogen, preferably $R^1$ is hydrogen;

$R^2$ is suitably methyl or hydrogen, preferably $R^2$ is hydrogen;

$R^3$ is suitably methyl or hydrogen, preferably $R^3$ is hydrogen;

$R^4$ is suitably hydrogen, $C_{1-6}$alkyl or $C_{1-6}$alkyloxy, preferably $R^4$ is hydrogen;

when $R^5$ and $R^6$ designate $R^{5a}$ and $R^{6a}$,
  then $R^{5a}$ and $R^{6a}$ suitably form a bivalent radical of formula (a1), (a2), (a3), (a4), (a7), (a8), (al 1) or (a12);
X is suitably O, S or $S(O)_2$, preferably X is O or $S(O)_2$;
Y is suitably O or S, preferably Y is O;
Z is suitably —O—C(O)— or —C(O)—O—;
when $R^5$ and $R^6$ designate $R^{5b}$ and $R^{6b}$,
  then $R^{6b}$ suitably is hydroxy$C_{1-6}$alkyl, trihalomethyl, or a radical of formula (b1), (b2), (b3), (b4), (b5), (b6) or (b13);

$R^{6b}$ preferably is in the 8-position of the dihydrobenzopyran moiety;

$R^8$ is suitably hydrogen or $C_{1-6}$alkyloxycarbonyl, preferably $R^6$ is hydrogen;

$R^9$ is suitably hydrogen or $C_{1-6}$alkyloxycarbonyl, preferably $R^7$ is hydrogen or methyloxycarbonyl;

$R^{10}$ and $R^{11}$ each independently are suitably hydrogen or $C_{1-6}$alkyl, preferably $R^{10}$ and $R^{11}$ are hydrogen or methyl;

$R^{12}$ and $R^{13}$ each independently are suitably hydrogen or hydroxy;

$R^{14}$ and $R^{15}$ each independently are suitably hydrogen or $C_{1-6}$alkyl, preferably $R^{14}$ and $R^{15}$ are hydrogen;

$R^{16}$ and $R^{17}$ each independently are hydrogen or $C_{1-6}$alkyl, preferably $R^{16}$ and $R^{17}$ are both hydrogen;

$R^{18}, R^{19}, R^{20}, R^{21}, R^{22}, R^{23}, R^{24}$ and $R^{25}$ are preferably hydrogen;

when $R^5$ and $R^6$ designate $R^{5c}$ and $R^{6c}$;
then $R^{5c}$ and $R^{6c}$ suitably are hydrogen, halo, or $C_{1-6}$alkyl, preferably $R^{5c}$ and $R^{6c}$ are hydrogen, chloro, fluoro, methyl or ethyl;

$Alk^1$ is suitably $C_{1-3}$alkanediyl, preferably $Alk^1$ is methylene;

$Alk^2$ is suitably $C_{2-6}$alkanediyl, preferably $Alk^2$ is 1,3-propanediyl;

when Q is a radical of formula (aa),
$R^{26}$ is suitably hydrogen, cyano, aminocarbonyl or methyl, preferably $R^{26}$ is hydrogen or cyano;
$R^{27}$ is suitably hydrogen or $C_{1-6}$-alkyl, preferably $R^{27}$ is hydrogen, methyl or ethyl;
$R^{28}$ is suitably hydrogen or $C_{1-6}$alkyl, preferably $R^{28}$ is hydrogen or methyl;

a radical of formula (bb),
$R^{29}$ and $R^{30}$ each independently are suitably hydrogen, hydroxy, halo, methyl, preferably both $R^{29}$ and $R^{30}$ are hydrogen or $R^{29}$ is hydrogen and $R^{30}$ is hydroxy;

a radical of formula (cc),
$R^{31}$ is suitably hydrogen, hydroxy, preferably $R^{31}$ is hydrogen;
$R^{32}$ is suitably hydrogen, or phenylmethyl, preferably $R^{32}$ is hydrogen;

a radical of formula (dd),
q is preferably 2;
$R^{33}$ and $R^{34}$ are both preferably hydrogen;
$R^{35}$ is suitably hydrogen or phenylmethyl, preferably $R^{35}$ is hydrogen;

a radical of formula (ee),
$R^{36}$ is suitably hydrogen, halo or methyl, preferably $R^{36}$ is hydrogen or chloro;
$R^{55}$ is suitably hydrogen or phenylmethyl;

a radical of formula (ff),
$R^{37}$ and $R^{38}$ each independently suitably are hydrogen, halo or methyl, preferably $R^{37}$ and $R^{38}$ are hydrogen or chloro;

a radical of formula (gg),
$R^{39}$ and $R^{40}$ each independently suitably are hydrogen, hydroxy, chloro or methyl, preferably $R^{39}$ and $R^{40}$ are both hydrogen or $R^{39}$ is hydrogen and $R^{40}$ is hydroxy;

a radical of formula (hh),
$R^{41}$ and $R^{42}$ each independently suitably are hydrogen, hydroxy, halo or methyl, preferably $R^{41}$ and $R^{42}$ are both hydrogen or $R^{41}$ is hydrogen and $R^{42}$ is chloro;

a radical of formula (ii),
$R^{43}$ and $R^{44}$ each independently suitably are hydrogen, halo, $C_{1-6}$alkyloxy, $C_{1-6}$alkylthio, amino, mono- or di($C_{1-6}$alkyl)amino, preferably $R^{43}$ is hydrogen, chloro, methylthio or amino and $R^{44}$ is hydrogen;

a radical of formula (jj),
$R^{45}$ and $R^{46}$ each independently suitably are hydrogen, halo, $C_{1-6}$alkyl, preferably $R^{45}$ and $R^{46}$ are hydrogen or chloro;

a radical of formula (kk),
r preferably is 2;
$R^{47}$ and $R^{48}$ both preferably are hydrogen;

a radical of formula (ll),
$R^{49}$ is suitably hydrogen or methyl, preferably hydrogen;

a radical of formula (mm),
$R^{50}$ and $R^{51}$ taken together suitably form a bivalent radical of formula $(CH_2)_4$;
$R^{52}$ suitably is hydrogen;

a radical of formula (nn),
$R^{53}$ is suitably hydrogen and $R^{54}$ suitably is hydroxy;
and aryl is preferably phenyl.

A group of special compounds are those compounds of formula (I) wherein $R^1$, $R^2$, $R^3$ and $R^4$ are as defined under formula (I) and wherein $R^5$ and $R^6$ designate $R^{5a}$ and $R^{6a}$, wherein in formulas (a7) and (a8) t is 2; Q is a radical of formula (aa), (bb), (cc), (dd) wherein q is 1 or 2, (ee) wherein $R^{55}$ is hydrogen, (ff), (gg), (hh), (ii), (jj), (kk) wherein q is 1 or 2, (ll).

Another group of special compounds are those compounds of formula (I) wherein $R^1$, $R^2$, $R^3$ are as defined under formula (I), $R^4$ is hydrogen, halo, $C_{1-6}$alkyl; $R^5$ and $R^6$ designate $R^{5b}$ and $R^{6b}$, $R^{5b}$ being hydrogen and $R^{6b}$ is hydroxy$C_{1-6}$alkyl, carboxyl$C_{1-6}$alkyl, $C_{1-6}$alkyloxycarbonyl$C_{1-6}$alkyl, trihalomethyl, a radical of formula (b1), (b2), (b3), (b4), (b5), (b6), (b7), (b8), (b9), (b10), (b11), (b12); Q is a radical of formula (aa), (bb), (cc), (dd) wherein q is 1 or 2, (ee) wherein $R^{55}$ is hydrogen, (ff), (gg), (hh), (ii), (jj), (kk) wherein q is 1 or 2, or (ll).

Still another group of special compounds are those compounds of formula (I) wherein $R^1$, $R^2$, $R^3$ are as defined under formula (I), $R^4$ is hydrogen and $R^5$ and $R^6$ designate $R^{5c}$ and $R^{6c}$, and Q is a radical of formula (gg); (hh); (ii); (jj); (kk) wherein q is 1 or 2; (ll); a radical of formula (bb) wherein $R^{29}$ is hydroxy on a carbon atom adjacent to a nitrogen atom; or a radical of formula (dd) wherein $R^{35}$ is hydrogen and $R^{33}$ and $R^{34}$ taken together with the carbon atom to which they are attached form C(O) and q is 1 or 2.

Interesting compounds are those compounds of formula (I), wherein $R^2$ is hydrogen.

Also interesting compounds are those compounds of formula (I) wherein $R^3$ is hydrogen.

Particular compounds are those compounds of formula (I) wherein $R^5$ and $R^6$ designate $R^{5a}$ and $R^{6a}$ and Q is a radical of formula (bb) wherein $R^{29}$ and $R^{30}$ are hydrogen; or Q is a radical of formula (dd) wherein q is 1 or 2 and $R^{31}$ and $R^{32}$ are both hydrogen.

Also particular compounds are those compounds of formula (I) wherein $R^5$ and $R^6$ designate $R^{5b}$ and $R^{6b}$, $R^{5b}$ being hydrogen and $R^{6b}$ is $C_{1-6}$alkyloxycarbonyl-$C_{1-6}$alkyl, trihalomethyl, $C_{1-6}$alkyloxycarbonyl-$C_{1-6}$alkyl-S—, $C_{1-6}$alkyl-S—, aryl-S—, aryl-S(O)—, or $R^{6b}$ is a radical of formula (b1), wherein $R^8$ is hydrogen; (b2) wherein $R^9$ is $C_{1-6}$alkyloxycarbonyl; (b3) wherein $R^{10}$ and $R^{11}$ both being hydrogen; (b4) wherein $R^{12}$ and $R^{13}$ are both hydrogen; (b5) wherein $R^{14}$ and $R^{15}$ are both hydrogen; (b6) $R^{16}$ is hydrogen or halo and $R^{17}$ is hydrogen; or (b13) wherein $R^{25}$ is hydrogen; Q is a radical of formula (bb) wherein $R^{29}$ and $R^{30}$ are hydrogen; or Q is a radical of formula (dd) wherein q is 1 or 2 and $R^{31}$ and $R^{32}$ are both hydrogen.

Still other particular compounds are those compounds of formula (I) wherein $R^4$ is hydrogen; $R^5$ and $R^6$ designate $R^{5c}$ and $R^{6c}$, $R^{5c}$ being hydrogen and $R^{6c}$ is hydrogen, halo, $C_{1-6}$alkyl or $C_{1-6}$alkyloxy; Q is a radical of formula (aa) wherein $R^{26}$ is hydrogen, cyano or aminocarbonyl, $R^{27}$ is aryl$C_{1-6}$alkyl and $R^{28}$ is hydrogen or $C_{1-6}$alkyl, or $R^{27}$ and $R^{28}$ taken together with the nitrogen atom to which they are attached form are piperazine ring which is N-substituted with $C_{1-6}$alkyl; a radical of formula (bb) wherein $R^{29}$ is hydroxy on a carbon atom adjacent to a nitrogen atom; a radical of formula (dd) wherein $R^{35}$ is hydrogen and $R^{33}$ and $R^{34}$ taken together with the carbon atom to which they are attached form C(O); a radical of formula (ee) wherein $R^{36}$ is hydroxy and $R^{55}$ is aryl$C_{1-6}$alkyl; a radical of formula (gg) wherein $R^{39}$ and $R^{40}$ each independently are hydrogen, $C_{1-6}$alkyl or aminocarbonyl; a radical of formula (hh) wherein $R^{41}$ and $R^{42}$ each independently are hydrogen, halo, hydroxy, $C_{1-6}$alkyl or aminocarbonyl; a radical of formula (ii) wherein $R^{44}$ is hydrogen and $R^{43}$ is hydrogen, $C_{1-6}$alkyloxy, $C_{1-6}$alkylthio, amino, mono- or di($C_{1-6}$alkyl) amino, piperidinyl; a radical of formula (jj) wherein $R^{45}$ and $R^{46}$ are both hydrogen; a radical of formula (kk) wherein $R^{47}$ and $R^{48}$ are both hydrogen; a radical of formula (ll) wherein $R^{49}$ is hydrogen; a radical of formula (mm) wherein $R^{50}$ is hydrogen, $R^{51}$ is hydroxy or $R^{50}$ and $R^{51}$ taken together form a bivalent radical of formula $(CH_2)_4$ and $R^{52}$ is hydrogen; or a radical of formula (nn) wherein $R^{53}$ is hydrogen and $R^{54}$ is hydroxy.

Preferred compounds are:
N-[(2,3,4,7,8,9-hexahydrobenzo[2,1-b:3,4-b']dipyran-2-yl) methyl]-N'-2-pyrimidinyl-1,3-propanediamine; N-[(2,3,4,7,8,9-hexahydrocyclopenta[h]-1-benzopyran-2-yl) methyl]-N'-2-pyrimidinyl-1,3-propanediamine; (±)-N-[(2,3,4,8,9, 10-hexahydrobenzo[2,1-b:3,4-b']dipyran-2-yl)methyl]-N'-2-pyrimidinyl-1,3-propane diamine; N-[(3,4,7,8,9,10-hexahydro-2H-naphtho[1,2-b]pyran-2-yl) methyl]-N'-2-pyrimidinyl-1,3-propanediamine; N-(4,5-dihydro-1H-imidazol-2-yl)-N'-[(2,3,4,7,8,9-hexahydrocyclopenta[h]-1-benzopyran-2-yl)methyl]-1,3-propanediamine; N-[(2,3,4,7,8,9-hexahydrobenzo[2,1-b:3,4-b']dipyran-2-yl)methyl]-N'-(1,4,5,6-tetrahydro-2-pyrimidinyl)-1,3-propanediamine; N-[(2,3,4,7,8,9-hexahydro cyclopenta[h]-1-benzopyran-2-yl)methyl]-N'-(1,4,5,6-tetrahydro-2-pyrimidinyl)-1,3-propanediamine; N-[(2,3,7,8-tetrahydro-9H-pyrano[2,3-f]-1,4-benzodioxin-9-yl)methyl]-N'-(1,4,5,6-tetrahydro-2-pyrimidinyl)-1,3-propanediamine; N-[(3,4,7,8,9, 1 0-hexahydro-2H-naphtho[1,2-b]pyran-2-yl)methyl]-N'-(1,4,5,6-tetrahydro-2-pyrimidinyl)-1,3-propanediamine; methyl 3-[6-fluoro-3,4-dihydro-2-[[[3-(2-pyrimidinylamino)propyl]amino]methyl]-2H-1-benzopyran-8-yl]-2-propenoate; N-[[6-fluoro-8-(2-furanyl)-3,4-dihydro-2H-1-benzopyran-2-yl]methyl]-N'-2-pyrimidinyl-1,3-propanediamine; N-[[6-fluoro-3,4-dihydro-8-(2-thienyl)-2H-1-benzopyran-2-yl]methyl]-N'-(1,4,5,6-tetrahydro-2-pyrimidinyl)-1,3-propanediamine; N-[(3,4-dihydro-2H-1-benzopyran-2-yl)methyl]-N'-(3,4,5,6-tetrahydro-2-pyridinyl)-1,3-propanediamine; $N^4$-[3-[ [(3,4-dihydro-2H-1-benzopyran-2-yl)methyl]amino] propyl]-$N^2$-methyl-2,4-pyrimidinediamine, the pharmaceutically acceptable acid addition salts thereof and the stereochemically isomeric forms thereof.

The compounds of formula (I) can generally be prepared by reacting a diamine of formula (II) with a reagent of formula (III) wherein $W^1$ is a reactive leaving group such as, for example, halo, e.g. chloro, bromo; alkyloxy, e.g. methoxy, ethoxy and the like; aryloxy, e.g. phenoxy and the like; alkylthio, e.g. methylthio, ethylthio and the like; arylthio, e.g. benzenethio and the like.

In the formulas (II), (III) and all the following formulas the variabels $R^1$, $R^2$, $R^3$, $R^4$, $R^5$, $R^6$, Alk$^1$, Alk$^2$, and Q are as defined under formula (I) unless specifically described otherwise.

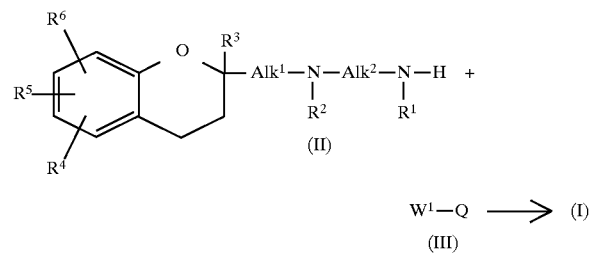

Said reaction can be performed by stirring the diamine of formula (II) with the reagent of formula (III) in an appropriate solvent such as, for example, an alcohol, e.g. ethanol and the like; a halogenated hydrocarbon, e.g. trichloromethane and the like or an ether, e.g. tetrahydrofuran, 1,4-dioxane and the like; an aromatic hydrocarbon, e.g. methylbenzene and the like or mixtures thereof. Optionally a base, such as, for example, an alkalimetal carbonate, e.g. sodium or potassium carbonate; an alkalimetal hydrogen carbonate, e.g. sodium or potassium hydrogen carbonate ; an appropriate organic base, e.g. N,N-diethylethanamine, pyridine and the like bases, can be added to pick up the acid that may be formed during the course of the reaction. Elevated temperatures may enhance the rate of the reaction. Preferably the reaction is performed at the reflux temperature of the reaction mixture.

The compounds of formula (I) can also generally be prepared by reductive N-alkylation of an aminoderivative of formula (VI) with an appropriate aldehyde of formula (V), wherein Alk$^3$ is a direct bond or $C_{1-4}$alkanediyl.

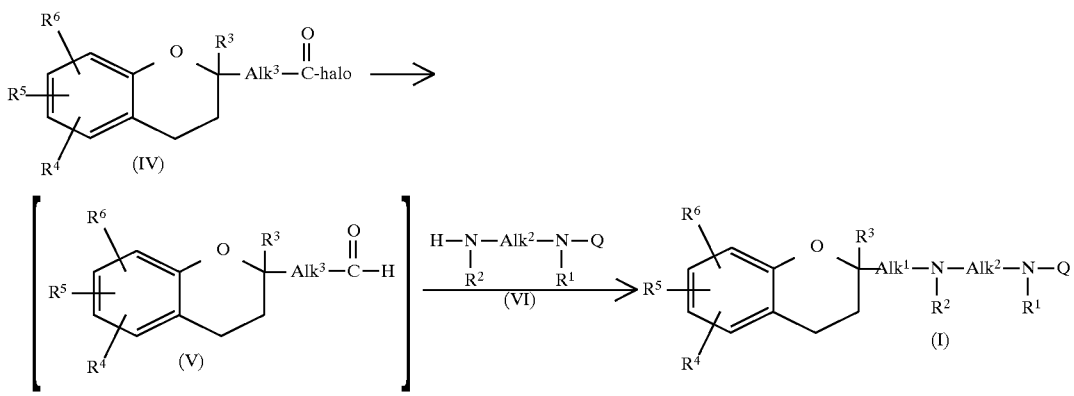

Said reaction is performed by stirring the reactants in an appropriate solvent such as, for example, an alcohol, e.g. ethanol and the like; an ether, e.g. tetrahydrofuran and the like; an aromatic solvent, e.g. methylbenzene and the like, or mixtures thereof. Optionally a water separator can be used to remove the water that is formed during the course of the reaction. The resulting imine can then be reduced by reactive hydride reagents such as, for example, sodium borohydride, or by catalytic hydrogenation on an appropriate catalyst, such as, for example palladium on charcoal, platinum on charcoal, Raney nickel and the like in a suitable solvent, such as, for example an alcohol, e.g. methanol, ethanol and the like; an ether, e.g. tetrahydrofuran, and the like; a carboxylic ester, e.g. ethyl acetate, butyl acetate and the like; or a carboxylic acid, e.g. acetic acid, propanoic acid and the like. Optionally the reaction may be performed at elevated temperatures and/or pressures.

The intermediate aldehyde of formula (V) can be prepared by reducing an acyl derivative of formula (IV) wherein $Alk^3$ is defined as above. The acyl halide can be prepared by reacting the corresponding acid, with a halogenating reagent such as thionylchloride, phosphorus trichloride, phosphorus tribromide, oxalylchloride and the like. The latter reaction may be performed in an excess of the halogenating reagent or in appropriate solvents such as for example halogenated hydrocarbons, e.g. dichloromethane, trichloromethane and the like; aromatic hydrocarbons, e.g. methylbenzene and the like; ethers, e.g. tetrahydrofuran, 1,4-dioxane and the like, or dipolar aprotic solvents, e.g. N,N-dimethylformamide, N N-dimethylacetamide and the like. Stirring and elevated temperatures may be appropriate to enhance the rate of the reaction.

Said reduction of the acylhalide of formula (IV) can for instance be performed by catalytic hydrogenation with a catalyst such as palladium on charcoal, palladium on bariumsulfate, platinum on charcoal and the like in appropriate solvents such as, for example ethers, e.g. tetrahydrofuran and the like; preferably in admixture with a dipolar aprotic solvent, such as, for example N,N-dimethylformamide, N,N-dimethylacetamide and the like. Optionally a catalyst poison can be added, such as thiophene, quinoline-sulfur and the like.

The reaction sequence starting from the intermediate of formula (IV) and yielding compounds of formula (I) may be performed as a one-pot procedure. The intermediates of formula (V) wherein $R^5$ and $R^6$ designate $R^{5a}$ and $R^{6a}$ are defined as intermediates of formula (V-a); intermediates of formula (V) wherein $R^5$ and $R^6$ designate $R^{5b}$ and $R^{6b}$ are defined as intermediates of formula (V-b). The intermediates of formula (V-a) and (V-b) are deemed novel.

The compounds of formula (I) can also be prepared by reductive N-alkylation of an amine of formula (IX) with an aldehyde of formula (X), wherein $Alk^4$ is $C_{2-14}$alkanediyl. The reaction conditions are similar to those described for the reaction of intermediates of formula (V) with those of formula (VI).

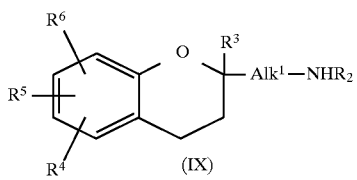

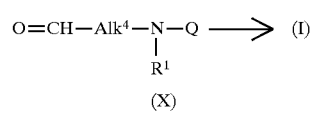

The intermediates of formula (IX) wherein $R^5$ and $R^6$ designate $R^{5a}$ and $R^{6a}$ are indicated hereinunder as intermediates of formula (IX-a); intermediates of formula (IX) wherein $R^5$ and $R^6$ designate $R^{5b}$ and $R^{6b}$ are indicated hereinunder as intermediates of formula (IX-b). The intermediates of formula (IX-a) and (IX-b) are deemed novel.

The compounds of formula (I) can also be prepared by N-alkylating an amine of formula (VI) with an intermediate of formula (VII), wherein $W^2$ is a reactive leaving group such as, for example, halo, e.g. chloro, bromo or iodo; sulfonyloxy, e.g. methanesulfonyloxy, methylbenzenesulfonyloxy and the like, in appropriate solvents such as ketones, e.g. 2-butanone and the like; ethers, e.g. tetrahydrofuran and the like; aromatic hydrocarbons, e.g. methylbenzene and the like; dipolar aprotic solvents, e.g. N,N-dimethylformamide, N,N-dimethylacetamide, dimethylsulfoxide and the like.

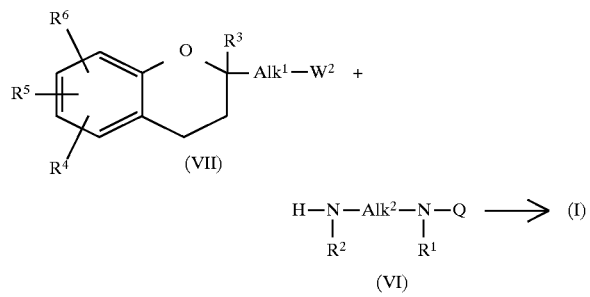

Stirring and heating may enhance the reaction rate. Optionally a suitable base may be added to pick up the acid that is formed during the course of the reaction, such as, for example an alkali metal carbonate, e.g. sodium or potassium carbonate; an alkali metal hydrogen carbonate, e.g. sodium or potassium hydrogen carbonate and the like; an appropriate organic base, e.g. N,N-diethylethanamine, pyridine and the like.

The intermediates of formula (VII) wherein $R^5$ and $R^6$ designate $R^{5a}$ and $R^{6a}$ are indicated hereinunder as intermediates of formula (VII-a); intermediates of formula (VII) wherein $R^5$ and $R^6$ designate $R^{5b}$ and $R^{6b}$ are indicated hereinunder as intermediates of formula (VII-b). The intermediates of formula (VII-a) and (VII-b) are deemed novel.

The compounds of formula (I), wherein $R^2$ is hydrogen, said compounds being represented by formula (I'), may be prepared by debenzylation of an intermediate of formula (VIII).

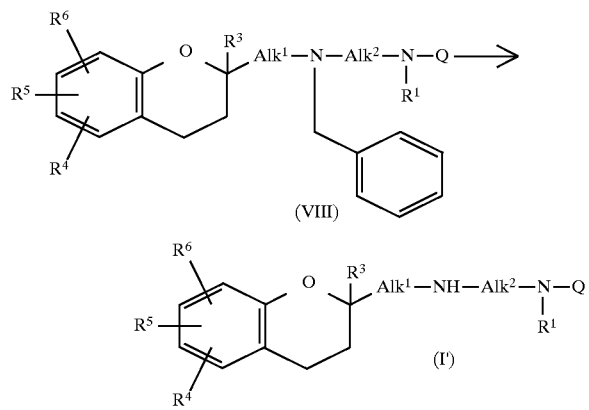

Said debenzylation can be performed following art-known procedures such as catalytic hydrogenation using appropriate catalysts, e.g. platinum on charcoal, palladium on charcoal, in appropriate solvents such as alcohols, e.g. methanol, ethanol, 2-propanol and the like; ethers e.g. 1,1'-oxybisethane, tetrahydrofuran, 2,2'-oxybispropane and the like. Optionally elevated temperatures and pressures may be applied.

Compounds of formula (I) wherein $R^5$ and $R^6$ designate $R^{5b}$ and $R^{6b}$ are indicated as compounds of formula (I-b). Compounds of formula (I-b) may be prepared by aromatic substitution of a halosubstited, preferably iodosubstituted, dihydrobenzopyran derivative of formula (XI). Said aromatic substitution may, for instance, be carried out with a reagent of formula (XII) in suitable solvent and in the presence of an appropriate catalyst, such as, for example, tetrakis(triphenylphosphine)palladium.

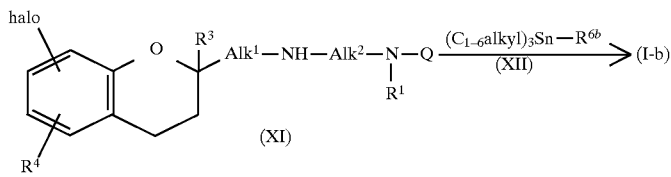

The compounds of formula (I), can also be converted into each other by functional group transformations. For instance the compounds of formula (I), wherein Q represents a pyrimidinyl or a pyridinyl moiety can be converted into the tetrahydroanalogs following art-known catalytic hydrogenation procedures. Furthermore, compounds of formula (I) bearing a $C_{3-6}$alkynyl group or $C_{3-6}$alkenyl group can be converted into the corresponding compounds bearing $C_{1-6}$alkyl group following art-known hydrogenation techniques. Compounds of formula (I) bearing a cyano group can be converted into the corresponding compounds bearing an aminomethyl substituent following art-known hydrogenation techniques. Compounds bearing an alkyloxy substituent can be converted into compounds bearing a hydroxy group by treating the alkyloxy compound with an appropriate acidic reagent such as for example, hydrohalic acid, e.g. hydrobromic acid or borontribromide and the like. Compounds bearing an amino substituent can be N-acylated or N-alkylated following art-known N-acylation or N-alkylation procedures.

The intermediates mentioned hereinabove are novel and may be prepared following art-known procedures which are for instance illustrated in the experimental part.

Pure stereochemically isomeric forms of the compounds of this invention may be obtained by the application of art-known procedures. Diastereoisomers may be separated by physical separation methods such as selective crystallization and chromatographic techniques, e.g. liquid chromatography. Enantiomers may be separated from each other by the selective crystallization of their diastereomeric salts with optically active acids. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable acid-addition salts and stereochemically isomeric forms thereof have interesting pharmacological properties: they show $5HT_{1-like}$ agonistic activity. The compounds of the present invention have remarkable vasoconstrictor activity. They are useful to prevent or treat conditions which are related to vasodilatation. For instance, they are useful in the treatment of conditions characterized by or associated with cephalic pain, e.g. cluster headache and headache associated with vascular disorders, especially migraine. These compounds are also useful in the treatment of venous insufficiency and in the treatment of conditions associated with hypotension.

The vasoconstrictor activity of the compounds of formula (I) can be determined using an in vitro-test as is described in "Instantaneous changes of alpha-adrenoreceptor affinity caused by moderate cooling in canine cutaneous veins" in the American Journal of Physiology 234(4), H330-H337, 1978; or in the test described in the pharmacological example, wherein the serotonin-like response of the compounds of the present invention was tested on the basilar arteries of pigs.

In view of their useful pharmacological properties, the subject compounds may be formulated into various pharmaceutical forms for administration purposes. To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employee For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of the present invention therefore may be used as medicines in conditions related to vasodilatation, more in particular hypotension, venous insufficiency and especially cephalic pain among which migraine. The compounds of the present invention also provide a method of treating warm-blooded animals suffering from conditions related to vasodilatation, such as, hypotension, venous insufficiency and especially cephalic pain among which migraine by administering an effective amount of a compound of formula (I), a pharmaceutically acceptable acid addition salt or a stereoisomeric form thereof. Those skilled in the art could easily determine the effective amount from the test results presented hereinafter. In general it is contemplated that an effective amount would be from 1 µg/kg to 1 mg/kg body weight, and in particular from 2 µg/kg to 200 µg/kg body weight. It may be appropriate to administer the required dose as two, three, four or more sub-doses at appropriate intervals throughout the day. Said sub-doses may be formulated as unit dosage forms, for example, containing 0.005 to 20 mg, and in particular 0.1 mg to 10 mg of active ingredient per unit dosage form.

The following examples are intended to illustrate and not to limit the scope of the present invention in all its aspects.

EXPERIMENTAL PART

A. Preparation of compounds of formula (I) wherein $R^5$ and $R^6$ designate $R^{5a}$ and $R^{6a}$ and the intermediates thereof.

EXAMPLE 1-a a) A mixture of 2,3-dihydro-1H-inden-4-ol (0.37 mol) and acetic anhydride (0.37 mol) in sulfuric acid (300 ml) was stirred for 1 hour at room temperature. The reaction mixture was poured out into a mixture of water and 1,1'-oxybisethane. The organic layer was separated, dried ($MgSO_4$), filtered and the solvent was evaporated, yielding 75 g (>100% crude residue) of 2,3-dihydro-1H-inden-4-ol acetate (ester) (interm. 1-a).

b) Intermediate (1-a) (0.37 mol) was heated to 100° C. Aluminum chloride (200 g) was added and the reaction mixture was stirred for 1 hour at 120° C. The reaction mixture was cooled and ice was added, followed by a mixture of water and concentrated hydrochloric acid. This mixture was extracted with 1,1'-oxybisethane. The organic layer was separated, treated with activated charcoal, dried ($MgSO_4$), filtered and the filtrate was evaporated. The residue was purified by distillation (oil pump; 110° C.), yielding 29 g of 1-(2,3-dihydro-4-hydroxy-1H-inden-5-yl)ethanone (interm. 2-a).

c) Sodium methylate (24 g) was stirred in methylbenzene (300 ml). A mixture of diethyl oxalate (0.16 mol) and intermediate (2-a) (0.16 mol) in methylbenzene (10 ml) was added dropwise. This mixture was stirred and refluxed for 2 hours. The resulting precipitate was filtered off and dried. The solid was stirred in a mixture of hydrochloric acid (10 ml) and acetic acid (500 ml). The reaction mixture was stirred and refluxed for 1 hour. The mixture was poured out into water. The resulting precipitate was filtered off and dried (vacuum), yielding 21 g of 4,7,8,9-tetrahydro-4-oxocyclopenta[h]-1-benzopyran-2-carboxylic acid (interm. 3-a).

d) A mixture of intermediate (3-a) (0.09 mol) in acetic acid (200 ml) was hydrogenated with palladium on activated carbon (1 g) as a catalyst. After uptake of hydrogen (3 eq.), the catalyst was filtered off. The solvent was evaporated. The residue was vacuum dried, yielding 21 g of (±)-2,3,4,7,8,9-hexahydrocyclopenta[h]-1-benzopyran-2-carboxylic acid (interm. 4-a).

e) A mixture of intermediate (4-a) (0.11 mol) in tetrahydrofuran (250 ml) was stirred under nitrogen flow. 1,1'-Carbonylbis-1H-imidazole (0.11 mol) was added and the reaction mixture was stirred for 2 hours at room temperature. Then, it was cooled to −80° C. A solution of diisobutylaluminum hydride in methyl benzene (20%) (0.33 mol) was added dropwise and the reaction mixture was stirred for 2 hours at −80° C. The mixture was decomposed with methanol, then poured out into water. The mixture was acidified, then extracted with 1,1'-oxybisethane. The separated organic layer was dried ($MgSO_4$), filtered and the solvent was evaporated, yielding 12 g of (±)-2,3,4,7,8,9-hexahydrocyclopenta[h]-1-benzopyran-2-carboxaldehyde (interm. 5-a).

In a similar manner were also prepared:

(±)-2,3,7,8-tetrahydro-9H-pyrano[2,3-f]-1,4-benzodioxin-9-carboxaldehyde (interm. 6-a);

(±)-2,3,4,8,9,10-hexahydrobenzo[1,2-b:3,4-b']dipyran-2-carboxaldehyde (interm. 7-a);

(±)-2,3,4,7,8,9-hexahydrobenzo[2,1-b:3,4-b']dipyran-2-carboxaldehyde (interm. 8-a).

EXAMPLE 2-a a) A mixture of 4-oxo-4H-naphto[1,2-b]pyran-2-carboxylic acid (12 g) and 2-methoxyethanol (100 ml) was hydrogenated at normal pressure and at room temperature in the presence of palladium on activated carbon 10% (2 g) as a catalyst. After the calculated amount of hydrogen was taken up, the catalyst was filtered off and the filtrate was evaporated, yielding 7 g (61.4%) of 3,4-dihydro-2H-naphto[1,2-b]pyran-2-carboxylic acid (interm. 9-a).

b) A mixture of intermediate (9-a) (7 g), ethanol (160 ml) and sulfuric acid was stirred and refluxed for 1 hour. The reaction mixture was evaporated and the oily residue was taken up in water. After treating with sodium hydroxide, the product was extracted with dichloromethane. The extract was dried, filtered and evaporated, yielding 5 g (63.5%) of ethyl 3,4-dihydro-2H-naphto[1,2-b]pyran-2-carboxylate (interm. 10-a).

c) A mixture of intermediate (10-a) (0.03 mol) in methanol saturated with ammonia (200 ml) was stirred at room temperature overnight. The precipitate was filtered off and washed with methanol. The product was used without further purification, yielding 6.6 g (97%) of (±)-3,4-dihydro-2H-naphtho[1,2-b]pyran-2-carboxamide (interm. 11-a).

d) A mixture of intermediate (11-a) (0.0291 mol) and sodium borohydride (0.1455 mol) in 1,4-dioxane (50 ml) was cooled till 0° C. under nitrogen. Acetic acid (0.1455 mol) in 1,4-dioxane (20 ml) was added dropwise and the mixture was stirred and refluxed for 2 hours 30 min. The mixture was evaporated till dryness. Water was added to the residue.

The mixture was acidified with concentrated HCl and stirred for 30 min. The mixture was basified with a 50% NaOH solution and extracted with dichloromethane. The organic layer was dried, filtered off and evaporated till dryness. The residue was converted into the hydrochloric acid salt and then liberated. The residue (29 g) was purified by column chromatography over silica gel (eluent: $CH_2Cl_2$/$CH_3OH$ 9.75/0.25). The pure fractions were collected and evaporated, yielding 2.4 g (39%) (±)-3,4-dihydro-2H-naphtho[1,2-b]pyran-2-methanamine (interm. 12-a).

In a similar manner was also prepared:

(±)-3,4,7,8,9,10-hexahydro-2H-naphtho[1,2-b]pyran-2-methanamine (interm. 13-a).

EXAMPLE 3-a

A mixture of intermediate (5-a) (0.03 mol) and benzenemethanamine (0.073 mol) in 2,2'-oxybispropane (250 ml) and N N-dimethylacetamide (10 ml) was hydrogenated with palladium on activated carbon (10%) (1 g) as a catalyst. After uptake of hydrogen (1 eq.), the catalyst was filtered off. The filtrate was evaporated. The residue was stirred in a mixture of water and 1, 1'-oxybisethane. The organic layer was separated, dried (MgSO$_4$), filtered and the solvent was evaporated, yielding 6.5 g of (±)-2,3,4,7,8,9-hexahydro-N-(phenylmethyl)cyclopenta[h]-1-benzopyran-2-methanamine (interm. 14-a).

EXAMPLE 4-a

A mixture of intermediate (14-a) (0.02 mol) and 2-propenenitrile (0.2 mol) in ethanol (100 ml) was stirred and refluxed overnight. The solvent was evaporated. The residue was dissolved in methanol. Palladium on activated carbon (10%) (2 g) was added and the mixture was hydrogenated. After uptake of hydrogen (3 eq.), the catalyst was filtered off and the filtrate was evaporated, yielding 5.2 g of (±)-N-[(2,3,4,7,8,9-hexahydrocyclopenta[h]-1-benzopyran-2-yl)methyl]-1,3-propanediamine (interm. 15-a).

EXAMPLE 5-a

A solution of ethyl 6-oxo-2,3-dimethyl-6H-furo[3,2-h][1]benzopyran-8-carboxylate (0.1 mol) in methanol (250 ml) was hydrogenated for 10 hours at 170° C. (pressurized) with palladium on activated carbon, palladium content 5% (2 g) as a catalyst in the presence of a 4% thiophene solution (10 ml). After uptake of hydrogen (3 equiv), the catalyst was filtered off and the filtrate was evaporated. The residue was purified by flash column chromatography over silica gel (eluent: CH$_2$Cl$_2$). The desired fractions were collected and the solvent was evaporated, yielding 20 g (72.9%) of (±)-ethyl 7,8-dihydro-2,3-dimethyl-6H-furo[3,2-h][1]benzopyran-8-carboxylate (interm. 16-a).

EXAMPLE 6-a

A mixture of intermediate (8-a) (6.9 g impure solid) and N-2-pyrimidinyl-1,2-propanediamine (0.02 mol) in methanol (200 ml) was hydrogenated with palladium on activated carbon (10%) (2 g) as a catalyst in the presence of a solution of thiophene (4%) (1 ml). After uptake of hydrogen (1 eq.), the catalyst was filtered off. The filtrate was evaporated The residue was purified by column chromatography over silica gel (eluent: CH$_2$Cl$_2$/(CH$_3$OH/NH$_3$) 95/5). The pure fractions were collected and the solvent was evaporated. The residue was dissolved in 2-propanone and converted into the ethanedioic acid salt (1:2). The salt was filtered off and dried (vacuum; 60° C.), yielding 7.8 g (73.0%) of (±)-N-[(2,3,4,7,8,9-hexahydrobenzo[2,1-b:3,4-b']dipyran-2-yl)methyl]-N'-2-pyrimidinyl-1,3-propanediamine ethanedioate (1:2); mp. 190.4° C. (comp. 1-a).

EXAMPLE 7-a

A mixture of intermediate (13-a) (0.0088 mol) and 3-(2-pyrimidinylamino)propanal (0.0112 mol) in methanol (100 ml) was hydrogenated with palladium on activated carbon (10%) (1 g) as a catalyst at room temperature and 3 atm. in a Parr apparatus. After uptake of hydrogen (1 eq.), the catalyst was filtered off and the filtrate was evaporated till dryness. The residue was purified by column chromatography over silica gel (eluent: CH$_2$Cl$_2$/(CH$_3$OH/NH$_3$) 97/3). The almost pure fractions were collected and evaporated. The residue was purified again by HPLC over silica gel (eluent: CH$_2$Cl$_2$/(CH$_3$OH/NH$_3$) 95/5). The pure fractions were collected and evaporated, yielding 0.85 g (27%) of (±)-N-[(3,4,7,8,9,10-hexahydro-2H-naphtho[1,2-b]pyran-2-yl)methyl]-N'-2-pyrimidinyl-1,3-propanediamine; mp. 57.6° C. (comp. 5-a).

EXAMPLE 8-a

Intermediate 16-a (0.072 mol) was dissolved in methylbenzene (250 ml)/H (100 ml). The solution was cooled to −70° C. Diisobutylaluminium hydride, 1.5M solution in hexane (0.1 mol) was added dropwise and the mixture was stirred for 1 hour at −70° C. Methanol (15 ml) was added dropwise and the reaction mixture was allowed to warm to room temperature. The mixture was poured out into water, acidified with hydrochloric acid and extracted with diethyl ether. The separated organic layer was dried, filtered and the solvent evaporated. The residue was dissolved in methanol (150 ml). N-2-pyrimidinyl-1,3-propanediamine (0.06 mol) was added and the mixture was hydrogenated with palladium-on-charcoal (small amount) as a catalyst in the presence of thiophene, 4% solution (10 ml). After uptake of H$_2$ (1 equiv), the catalyst was filtered off and the filtrate was evaporated. The residue was purified by column chromatography over silica gel (eluent: CH$_2$Cl$_2$/CH$_3$OH 90/10). Three fraction groups were collected and the solvent was evaporated, yielding residues (1), (2) and (3) (12 g). A sample of residue (3) (3.6 g) was dissolved in 2-propanone and converted into the ethanedioic acid salt (1:2) with a solution of ethanedioic acid.H$_2$O (0.020 mol) in 2-propanone. The precipitate was filtered off and dried, yielding 4.5 g (46.1%) of (±)-N-[(7,8-dihydro-2,3-dimethyl-6H-furo[3,2-h][1]benzopyran-8-yl)methyl]-N'-2-pyrimidinyl-1,3-propanediamine ethanedioate(1:2); mp. 208.8° C. (comp. 7-a). Residue (2) was repurified by column chromatography over silica gel (eluent: CH$_2$Cl$_2$/CH$_3$OH 85/15). The desired fractions were collected and the solvent was evaporated. The residue (1.8 g) was dissolved in ethanol and converted into the ethanedioic acid salt (1:2) with ethanedioic acid (0.010 mol). The precipitate was filtered off and dried, yielding 1.1 g (3.3%) (±)-N-2-pyrimidinyl-N'-[(3,6,7,8-tetrahydro-2,3-dimethyl-2H-furo[3,2-h][1]benzopyran-8-yl)methyl]-1,3-propanediamine ethanedioate (1:2); mp. 171.2° C. (comp. 8-a).

The following compounds were prepared:

TABLE 2a

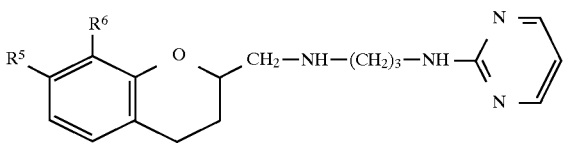

| Co. No. | Ex. No. | R$^5$, R$^6$ | Physical data |
|---|---|---|---|
| 1-a | 6-a | —CH$_2$—CH$_2$—CH$_2$—O— | mp. 190.4° C./.2(COOH)$_2$ |
| 2-a | 6-a | —CH$_2$—CH$_2$—CH$_2$— | mp. 118.2° C./.2 HCl.½H$_2$O |

TABLE 2a-continued

[Structure: chroman with R5, R6 substituents, O-CH2-NH-(CH2)3-NH linked to pyrimidine]

| Co. No. | Ex. No. | R⁵, R⁶ | Physical data |
|---|---|---|---|
| 3-a | 6-a | $-O-CH_2-CH_2-O-$ | mp. 199.0° C./.2(COOH)$_2$ |
| 4-a | 6-a | $-O-CH_2-CH_2-CH_2-$ | mp. 197.6° C./.2(COOH)$_2$.H$_2$O |
| 5-a | 7-a | $-CH_2-CH_2-CH_2-CH_2-$ | mp. 57.6° C. |
| 6-a | 7-a | $-CH=CH-CH=CH-$ | mp. 226.3° C./.(COOH)$_2$ |
| 7-a | 8-a | $-C(CH_3)=C(CH_3-O-$ | mp. 208.8° C./.(COOH)$_2$ |
| 8-a | 8-a | $-CH(CH_3)-CH(CH_3)-O-$ | mp. 171.2° C./.(COOH)$_2$ |
| 16-a | 6-a | $-O-CH_2-O-$ | mp. 169.3° C./.2(COOH)$_2$.½H$_2$O |

EXAMPLE 9-a

A mixture of intermediate (15-a) (0.02 mol) and 2-methylthioimidazole monohydrochloride (0.02 mol) in ethanol (100 ml) was stirred and refluxed for 16 hours. The solvent was evaporated. The residue was purified by column chromatography over silica gel (eluent: CH$_2$Cl$_2$/CH$_3$OH/(CH$_3$OH/NH$_3$) 90/9/1). The pure fractions were collected and the solvent was evaporated. The residue was dissolved in 2-propanol and converted into the hydrochloric acid salt (1:2) with HCl/2-propanol. The salt was filtered off and dried, yielding 2.4 g of (±)-N-(4,5-dihydro-1H-imidazol-2-yl)-N'-[(2,3,4,7,8,9-hexahydro cyclopenta[h]-1-benzopyran-2-yl)methyl]-1,3-propanediamine dihydrochloride hemihydrate; mp. 189.7° C. (comp. 9-a).

Example 10-a

A mixture of compound (1-a) (0.0099 mol) in methanol (300 ml) was hydrogenated with palladium on activated carbon (10%) (2 g) as a catalyst in the presence of a solution of thiophene (4%) (1 ml). After uptake of hydrogen (2 eq.), the catalyst was filtered off. The filtrate was evaporated and the residue was crystallized from methanol. The precipitate was filtered off and dried. This fraction was recrystallized from methanol. The precipitate was filtered off and dried, yielding 0.9 g (16.9%). The mother liquor was evaporated. The residue was dried, yielding 0.4 g (7.5%) (±)-N-[(2,3,4,7,8,9-hexahydrobenzo[2,1-b:3,4-b']dipyran-2-yl)methyl]-N'-(1,4,5,6-tetrahydro-2-pyrimidinyl)-1,3-propanediamine ethanedioate (1:2); mp. 226.9° C. (comp. 10-a).

B. Preparation of compounds of formula (I) wherein R⁵ and R⁶ designate R$^{5b}$ and R$^{6b}$ and the intermediates thereof

EXAMPLE 1-b a) 6-fluoro-3,4-dihydro-2H-1-benzopyran-2-methanol (0.093 mol) was dissolved in acetic acid (100 ml). Iodine monchloride (0.150 mol) was warmed to 35° C. and added as a fluid to the solution of 6-fluoro-3,4dihydro-2H-1-benzopyran-2-methanol in acetic acid. The reaction mixture was stirred and refluxed for 24 h. The mixture was cooled, poured out onto ice (200 ml) and this mixture was extracted with CH$_2$Cl$_2$. The separated organic layer was dried, filtered and evaporated. The residue was purified by flash column chromatography over silica gel (eluent: CH$_2$Cl$_2$). The desired fractions were collected and the solvent was evaporated, yielding: 23.6 g (72.2%) of (±)-6-fluoro-3,4-dihydro-8-iodo-2H-1-benzopyran-2-methanol acetate(ester) (interm. 1-b).

b) Intermediate 1-b (0.035 mol) was dissolved in N,N-diethylethanamine (250 ml). N$_2$ was allowed to bubble through the solution during 15 min. Bis (triphenylphosphine) palladium (II) chloride (0.00042 mol) and cuprous iodide (0.0015 mol) were added. Trimethylsilylacetylene (0.056 mol) was added and the reaction mixture was stirred for 30 min at 50° C. (under N$_2$ flow). The blackened mixture was cooled and the solvent was evaporated. The residue was dissolved in methanol saturated with ammonia (50 ml) and stirred TABLE 2-a

[Structure: chroman with R5, R6 substituents, O-CH2-NH-(CH2)3-NH linked to tetrahydropyrimidine ring with (CH2)q]

| Co. No. | Ex. No. | R⁵, R⁶ | q | Physical data |
|---|---|---|---|---|
| 9-a | 9-a | $-CH_2-CH_2-CH_2-$ | 1 | mp. 189.7° C./.2 HCl.½H$_2$O |
| 10-a | 10-a | $-CH_2-CH_2-CH_2-O-$ | 2 | mp. 226.9° C./.2(COOH)$_2$ |
| 11-a | 10-a | $-CH_2-CH_2-CH_2-$ | 2 | mp. 210.0° C./.2 HCl |
| 12-a | 10-a | $-O-CH_2-CH_2-O-$ | 2 | mp. 209.1° C./.2(COOH)$_2$ |
| 13-a | 10-a | $-CH_2-CH_2-CH_2-CH_2-$ | 2 | .2 HCl.2 H$_2$O |
| 14-a | 10-a | $-C(CH_3)=C(CH_3)-O$ | 2 | mp. 210.9° C./.2(COOH)$_2$ |
| 15-a | 10-a | $-CH(CH_3)=CH(CH_3)-O$ | 2 | mp. 206.4° C./.2(COOH)$_2$ |
| 17-a | 10-a | $-O-CH_2-O-$ | 2 | mp. 199.1° C./.2(COOH)$_2$ | for 4 hours at room temperature. The solvent was evaporated. The residue was purified by column chromatography over silica gel (eluent: $CH_2Cl_2/CH_3OH$ 97/3). The desired fractions (mixture of several compounds) were collected and the solvent was evaporated. The residue (7.1 g) was dissolved in dichloromethane (150 ml). N,N-diethylethanamine (15 ml) was added, followed by 4-methylbenzenesulfonyl chloride (0.035 mol) and the reaction mixture was stirred overnight at room temperature. Water (150 ml) was added. The organic layer was separated. The aqueous layer was washed with $CH_2Cl_2$ (150 ml). The combined organic layers were dried ($MgSO_4$), filtered and the solvent was evaporated. The residue was purified by column chromatography over silica gel (eluent: $CH_2Cl_2$). The pure fractions were collected and the solvent was evaporated, yielding 7.16 g (56.8%). This fraction was recrystallized from DIPE. The precipitate was filtered and dried, yielding 4.27 g (33.9%) of (±)-8-ethynyl-6-fluoro-3,4-dihydro-2H-1-benzopyran-2-methanol 4-methylbenzenesulfonate(ester); mp. 120.2° C. (interm. 2-b).

In a similar manner was also prepared:

(±)-methyl [3-6-fluoro-3,4-dihydro-2-[[[(4-methylphenyl)sulfonyl]oxy]methyl]-2H-1-benzopyran-8-yl]-2-propenoate (interm. 3-b).

EXAMPLE 2-b

A suspension of (±)-methyl 6-fluoro-3,4-dihydro-8-iodo-2H-1-benzopyran-2-carboxylate (0.026 mol), (trifluoromethyl)trimethylsilane (0.081 mol), cuprous iodide (0.1 mol) and kalium fluoride (0.081 mol) in a mixture of DMF (50 ml) and 1-methyl-2-pyrrolidinone (50 ml) was stirred for 3 h at 60° C. The cooled reaction mixture was poured out into a solution of iron (III) chloride (200 g) and hydrochloric acid (50 ml) in water (300 ml). This mixture was extracted three times with diethyl ether (150 ml). The combined organic layers were washed with a 5% aqueous $Na_2S_2O_3$ solution (decolorization), dried ($MgSO_4$), filtered and the solvent was evaporated. The residue was purified by flash column chromatography over silica gel (eluent: $CH_2Cl_2$). The pure fractions were collected and the solvent was evaporated, yielding 5.7 g (78.8%). This fraction was recrystallized from DIPE. The precipitate was filtered off and dried, yielding 1.2 g (16.6%) (±)-methyl 6-fluoro-3,4-dihydro-8-(trifluoromethyl)-2H-1-benzopyran-2-carboxylate; mp. 71.8° C. (interm 4-b).

EXAMPLE 3-b a) A solution of intermediate 1-b (0.022 mol), 2-tributylstannyl furan (0.024 mol) and tetrakis(triphenylphoshine)palladium (0.0005 mol) in 1-methyl-2-pyrrolidinone (50 ml) was stirred for 16 hours at 100° C. The cooled reaction mixture was poured out into water (200 ml) and this mixture was extracted with DIPE (200 ml). The separated organic layer was dried, filtered and the solvent was evaporated. The residue was stirred in methanol saturated with ammonia (50 ml) for 16 hours. The solvent was evaporated. The residue was purified by column chromatography over silica gel (eluent: $CH2Cl_2$/hexane 50/50, upgrading to pure $CH_2Cl_2$). The desired fractions were collected and the solvent was evaporated, yielding 4.5 g (82.4%) of (±)-6-fluoro-8-(2-furanyl)-3,4-dihydro-2H-1-benzopyran-2-methanol (interm. 5-b).

b) 4-methylbenzenesulfonyl chloride (0.021 mol) was added to a solution of intermediate 5-b (0.018 mol) in $CH_2Cl_2$ (50 ml). N,N-diethylethanamine (5 ml) was added and the reaction mixture was stirred for 24 hours at room temperature. The reaction mixture was poured out into water and this mixture was extracted with $CH_2Cl_2$. The separated organic layer was dried, filtered and the solvent was evaporated. The residue was purified by column chromatography over silica gel (eluent: $CH_2Cl_2$/hexane 50/50). The pure fractions were collected and the solvent was evaporated. The residue was stirred in DIPE and the white precipitate was filtered off and dried, yielding: 5.2 g (71.8%) of (±)-6-fluoro-8-(2-furanyl)-3,4-dihydro-2H-1-benzopyran-2-methanol 4-methylbenzenesulfonate(ester); mp. 110.4° C. (interm. 6-b).

In a similar manner were also prepared:

(±)-6-fluoro-3,4-dihydro-8-(2-thienyl)-2H-1-benzopyran-2-methanol 4-methylbenzene-sulfonate(ester) (interm. 7-b);

(±)-6-fluoro-3,4-dihydro-8-phenyl-2H-1-benzopyran-2-methanol 4-methylbenzenesulfonate(ester) (interm. 8-b);

(±)-6-fluoro-3,4-dihydro-8-(2-pyridinyl)-2H-1-benzopyran-2-methanol 4-methylbenzenesulfonate(ester) (interm. 9-b);

(±)-8-(ethylthio)-6-fluoro-3,4-dihydro-2H-1-benzopyran-2-methanol methanesulfonate(ester); mp. 107,7° C. (interm. 10-b); and (±)-6-fluoro-3,4-dihydro-8-(phenylthio)-2H-1-benzopyran-2-methanol methanesulfonate(ester) (interm. 11-b).

EXAMPLE 4-b

A solution of intermediate 11-b (0.016 mol) in dichloromethane (15 ml) was added dropwise to a mixture of $Al_2O_3$ (16 g; neutral, wet) and 2 $KHSO_5.KHSO_4.K_2SO_4$ (0.016 mol) in dichloromethane (65 ml). The reaction mixture was stirred overnight at room temperature. The reaction mixture was filtered, washed with $CH_2Cl_2$ and the filtrate was dried ($MgSO_4$), filtered and the solvent evaporated. The residue was purified by column chromatography over silica gel (eluent: $CH_2Cl_2/CH_3OH$ 97.5/2.5). The desired fractions were collected and the solvent was evaporated. The residue (7.2 g) was repurified by column chromatography over silica gel (eluent: $CH_2Cl_2$, upgrading to $CH_2Cl_2/(CH_3OH/NH_3)$ 50/50). The pure fractions were collected and the solvent was evaporated, yielding 3.8 g (61.8%) of (±)-6-fluoro-3,4-dihydro-8-(phenylsulfinyl)-2H-1-benzopyran-2-methanol methanesulfonate(ester) (interm. 12-b).

EXAMPLE 5-b a) (±)-Methyl 6-fluoro-3,4-dihydro-2H-1-benzopyran-2-carboxylate (0.26 mol) was added to stirred nitric acid (300 mol). The reaction mixture was stirred for 10 min at 40° C. The reaction mixture was stirred for 60 min at 60° C. The mixture was poured out into water. The resulting precipitate was filtered off. The filtrate was extracted with $CH_2Cl_2$. The separated organic layer was evaporated, leaving 33 g of residue, yielding 33 g of (±)-6-fluoro-3,4-dihydro-8-nitro-2H-1-benzopyran-2-carboxylic acid (interm. 13-b).

b) A 1M solution of $(CH_3)_2S.BH_3$ in dichloromethane (0.28 mol) was added dropwise to a mixture of intermediate 13-b (0.25 mol) in tetrahydrofuran (800 ml), stirred under $N_2$ flow. About 60 ml of the solvent was removed by distillation. The reaction mixture was stirred and refluxed for 2 h. The mixture was cooled, decomposed with $CH_3OH$ (20 ml), poured out into $H_2O$/NaOH and this mixture was extracted with $CH_2Cl_2$. The separated organic layer was washed with water, dried (MgSO$_4$), filtered and the solvent was evaporated, yielding 59 g of (±)-6-fluoro-3,4-dihydro-8-nitro-2H-1-benzopyran-2-methanol (104% crude residue) (interm. 14-b).

c) A mixture of intermediate 14-b (0.25 mol), 3,4-dihydro-2H-pyran (0.50 mol) and hydrochloric acid in 2-propanol (0.5 ml) in trichloromethane (700 ml) was stirred for 3 h on a water bath. The reaction mixture was washed with a 10% NaOH solution. The organic layer was separated, dried (MgSO$_4$), filtered and the solvent was evaporated, yielding 81 g of (±)-6-fluoro-3,4-dihydro-8-nitro-2-[[(tetrahydro-2H-pyran-2-yl)oxy]methyl]-2H-1-benzopyran (104% crude residue) (interm. 15-b).

d) A mixture of intermediate 15-b (0.47 mol) in methanol (600 ml) was hydrogenated with palladium on activated carbon, palladium content 10% (5 g) as a catalyst in the presence of a 4% thiophene solution (3 ml). After uptake of H$_2$ (3 equiv), the catalyst was filtered off and the filtrate was evaporated, yielding 130 g (98.3%) of (±)-6-fluoro-3,4-dihydro-2-[[(tetrahydro-2H-pyran-2-yl)oxy]methyl]-2H-1-benzopyran-8-amine (interm. 16-b).

e) A mixture of intermediate 16-b (0.036 mol), 2,5-dimethoxytetrahydrofuran (0.22 mol) and PTSA (catalytic quantity) in DMF (140 ml) was stirred for 90 min at 100° C. The solvent was evaporated. The residue was dissolved in CH$_2$Cl$_2$. The organic solution was washed once with water, dried (MgSO$_4$), filtered and the solvent was evaporated. The residue was purified by column chromatography over silica gel (eluent: CH$_2$Cl$_2$). The pure fractions were collected and the solvent was evaporated, yielding 6.6 g (55.3%) of (±)-6-fluoro-3,4-dihydro-8-(1H-pyrrol-1-yl)-2-[[(tetrahydro-2H-pyran-2-yl)oxy]-methyl]-2H-1-benzopyran (interm. 17-b).

f) A hydrochloric acid solution 10% (25 ml) was added to a mixture of intermediate 17-b (0.019 mol) in methanol (65 ml). The reaction mixture was stirred for 60 min at room temperature. The solvent was evaporated. The residue was partitioned between CH$_2$Cl$_2$ and H$_2$O. The organic layer was separated, dried (MgSO$_4$), filtered and the solvent was evaporated. The residue was purified over silica gel on a glass filter (eluent: CH$_2$Cl$_2$/CH$_3$OH 98/2). The pure fraction were collected and the solvent was evaporated, yielding: 3.4 g (72.4%) of (±)-6-fluoro-3,4-dihydro-8-(1H-pyrrol-1-yl)-2H-1-benzopyran-2-methanol (interm. 18-b).

g) N,N-diethylethanamine (7 ml) was added dropwise to a mixture of intermediate 18-b (0.024 mol) and methanesulfonyl chloride (0.035 mol) in 2-propanone (30 ml), stirred and cooled on an ice bath. The reaction mixture was stirred for 1 hour. The mixture was filtered and the filtrate was evaporated. The residue was dissolved in CH$_2$Cl$_2$. The organic solution was washed with an aqueous hydrochloric acid solution, dried (MgSO$_4$), filtered and the solvent was evaporated, yielding 7.6 g (97.3%) of (±)-6-fluoro-3,4-dihydro-8-(1H-pyrrol-1-yl)-2H-1-benzopyran-2-methanol methanesulfonate(ester) (interm. 19-b).

EXAMPLE 6-b

A solution of Br$_2$ (0.01 mol) in dichloromethane (50 ml) was added dropwise to a solution of (±)-6-fluoro-3,4-dihydro-8-(2-thienyl)-2H-1-benzopyran-2-methanol 4-methylbenzenesulfonate(ester) (0.01 mol) in dichloromethane (50 ml), stirred at 0° C. The reaction mixture was poured out into water. The organic layer was separated, dried, filtered and the solvent was evaporated. The residue was crystallized from DIPE. The precipitate was filtered off and dried, yielding 3.8 g (76.4%) of (±)-8-(5-bromo-2-thienyl)-6-fluoro-3,4-dihydro-2H-1-benzopyran-2-methanol 4-methylbenzenesulfonate(ester) (interm. 20-b).

EXAMPLE 7-b

Calcium oxide (5 g) was added to a solution of intermediate 2-b (0.0125 mol) and N-2-pyrimidinyl-1,3-propanediamine (0.019 mol) in tetrahydrofuran (100 ml) and the reaction mixture was stirred overnight at 150° C. (pressure vessel). The reaction mixture was cooled and filtered. The filtrate was evaporated. The residue was purified by column chromatography over silica gel (eluent: CH$_2$Cl$_2$, upgrading to CH$_2$Cl$_2$/CH$_3$OH 90/10). Two desired fractions were collected and the solvent was evaporated, yielding 1.2 g of the pure fraction. This fraction was dissolved in methanol (100 ml) and converted into the ethanedioic acid salt (1:1) with etanedioic acid hydrate (0.620 g). The mixture was concentrated, 2-propanone was added and the resulting precipitate was filtered off and dried, yielding 1.2 g (22.3%) of (±)-N-[(8-ethynyl-6-fluoro-3,4-dihydro-2H-1-benzopyran-2-yl)methyl]-N'-2-pyrimidinyl-1,3-propanediamine ethanedioate(1:1);

mp. 201.1° C. (comp. 1-b).

EXAMPLE 8-b

A solution of diisobutylaluminum hydride in methylbenzene (20%) (22 ml) was added dropwise to a solution of intermediate 4-b (0.018 mol) in methylbenzene (50 ml), stirred at −70° C. This mixture was stirred for 1 hour at −70° C. Methanol (10 ml) was added and the mixture was warmed to room temperature, poured out into water, acidified with HCl, then extracted with dichloromethane. The separated organic layer was evaporated. A mixture of the residue and N-2-pyrimidinyl-1,3-propanediamine (0.014 mol) was hydrogenated with palladium (2 g) as a catalyst in the presence of a solution of thiophene (4%) (2 ml). After uptake of hydrogen (250 ml), the catalyst was filtered off and the filtrate was evaporated. The residue was purified by column chromatography over silica gel (eluent: CH$_2$Cl$_2$/CH$_3$OH 90/10). The pure fractions were collected and the solvent was evaporated. The residue (2.2 g) was dissolved in ethanol (50 ml) and converted into the ethanedioic acid salt (1:1) with ethanedioic acid (0.024 mol). The precipitate was filtered off and dried. This fraction was recrystallized from methanol (±300 ml). The precipitate was filtered off and dried, yielding 0.950 g (13.6%) of (±)-N-[[6-fluoro-3,4-dihydro-8-(trifluoromethyl)-2H-1-benzopyran-2-yl]methyl]-N'-2-pyrimidinyl-1,3-propanediamine ethanedioate (1:1); mp. 216.3° C. (comp. 2-b).

EXAMPLE 9-b

A solution of the free base of compound (2-b) (0.00313 mol) and ethanedioic acid dihydrate (0.00635 mol) in methanol (50 ml) was hydrogenated for 2 hours at 50° C., with palladium on activated carbon (1 g) as a catalyst. After uptake of hydrogen (2 eq.), the catalyst was filtered off and the filtrate was concentrated. The resulting precipitate was filtered (*) off and dried, yielding 0.310 g (17.2%) of product. The corresponding (*) filtrate was treated with 2-propanone and the resulting precipitate was filtered off and dried, yielding 0.500 g (27.7%) of (±)-N-[[6-fluoro-3,4-dihydro-8-(trifluoromethyl)-2H-1-benzopyran-2-yl]- methyl]-N'-(1,4,5,6-tetrahydro-2-pyrimidinyl)-1,3-propanediamine ethanedioate (1:2). hemihydrate; mp. 177.1° C. (comp. 3-b).

EXAMPLE 10-b

Reaction under $N_2$ flow. A solution of $Bu_3SnSCH_2COOE_t$ (0.011 mol) in methylbenzene (40 ml) was added dropwise to a mixture of intermediate 1-b (0.011 mol) and tetrakis(triphenylphosphine)palladium (0.00029 mol) in methylbenzene (160 ml). The reaction mixture was stirred and refluxed overnight. The reaction mixture was cooled, washed with a 10% KF solution, dried ($MgSO_4$), filtered and the solvent was evaporated. The residue was purified over silica gel on a glass filter (eluent: $CH_2Cl_2/(CH_3OH/NH_3)$ 95/5). The desired fractions were collected and the solvent was evaporated. The residue was dissolved in 2-propanone and converted into the ethanedioic acid salt (1:2). The precipitate was filtered off and dried (vacuum; 60° C.), yielding 4.4 g (65.1%) of (±)-ethyl [[6-fluoro-3,4-dihydro-2-[[[3-(2-pyrimidinylamino)propyl]amino]methyl]-2H-1-benzopyran-8-yl]thio]acetate ethanedioate(1:2); mp. 154.4° C. (compound 17-b).

TABLE 1-b

| Co. No. | Ex. No. | $R^{6b}$ | Q | Physical data |
|---|---|---|---|---|
| 1-b | 1-b | —C≡CH | 2-pyrimidinyl | mp. 201.1° C./.(COOH)$_2$ |
| 2-b | 2-b | —CF$_3$ | 2-pyrimidinyl | mp. 216.3° C./.(COOH)$_2$ |
| 3-b | 3-b | —CF$_3$ | 1,4,5,6-tetrahydro-2-pyrimidinyl | mp. 177.1° C./.2 (COOH)$_2$. 1/2H$_2$O |
| 4-b | 1-b | —CH=CH—C(=O)OCH$_3$ | 2-pyrimidinyl | (E).2 (COOH)$_2$ |
| 5-b | 1-b | 2-furanyl | 2-pyrimidinyl | mp. 192.8° C./.2 (COOH)$_2$ |
| 6-b | 1-b | 2-thienyl | 2-pyrimidinyl | mp. 205.8° C./.³⁄₂(COOH)$_2$ |
| 7-b | 3-b | 2-thienyl | 1,4,5,6-tetrahydro-2-pyrimidinyl | mp. 216.8° C./.2 (COOH)$_2$ |
| 8-b | 1-b | 5-bromo-2-thienyl | 2-pyrimidinyl | mp. 191.5° C./.2 (COOH)$_2$ |
| 9-b | 3-b | —(CH$_2$)$_2$—C(O)—OCH$_3$ | 1,4,5,6-tetrahydro-2-pyrimidinyl | mp. 209.6° C./.2 (COOH)$_2$ |
| 10-b | 1-b | phenyl | 2-pyrimidinyl | mp. 159.2° C./.2 (COOH)$_2$ |
| 11-b | 1-b | 2-pyridinyl | 2-pyrimidinyl | mp. 158.9° C./ (E)-2-butenedioate(1:1) |
| 12-b | 1-b | —S—CH$_2$—CH$_3$ | 2-pyrimidinyl | mp. 160.6° C./2 (COOH)$_2$ |
| 13-b | 1-b | phenylthio | 2-pyrimidinyl | mp. 181.0° C./2 (COOH)$_2$ |
| 14-b | 1-b | phenylsulfinyl | 2-pyrimidinyl | mp. 129.4° C./2 (COOH)$_2$ |
| 15-b | 1-b | 1H-pyrrol-1-yl | 2-pyrimidinyl | mp. 162.1° C./2 (COOH)$_2$ |
| 16-b | 3-b | 1H-pyrrol-1-yl | 1,4,5,6-tetrahydro-2-pyrimidinyl | mp. 177.7° C./.2 (COOH)$_2$ |
| 17-b | 4-b | —S—CH$_2$—C(=O)—O—CH$_2$CH$_3$ | 2-pyrimidinyl | mp. 154.4° C./2 (COOH)$_2$ |

TABLE 1-b-continued

[Structure: benzopyran with R6b, O, R3, CH2-N(H)-(CH2)3-N(H)-Q, and F substituent]

| Co. No. | Ex. No. | R6b | Q | Physical data |
|---|---|---|---|---|
| 18-b | 3-b | 2-pyridinyl | [tetrahydropyrimidinyl structure: H-N-C=N with connecting chain] | mp. 186.3° C./.2 (COOH)₂ |

C. Preparation of the compounds of formula (I) wherein $R^5$ and $R^6$ designate $R^{5c}$ and $R^{6c}$ and the intermediates thereof.

EXAMPLE 1-c

A mixture of 3,6-dichloropyridazine (0.168 mol), 1,3-propanediamine (0.84 mol) and sodium carbonate (0.17 mol) in ethanol (500 ml) was stirred and refluxed overnight. The reaction mixture was filtered over dicalite. The filtrate was evaporated. The residue was crystallized from acetonitrile. The crystals were filtered off and dried, yielding 20.7 g of N-(6-chloro-3-pyridazinyl)-1,3-propanediamine; mp. 124.9° C. (interm. 1-c).

In a similar manner were also prepared:

N-3-pyridazinyl-1,3-propanediamine dihydrochloride; mp. 210.9° C. (interm. 2-c).

N-(6-methyl-3-pyridazinyl)-1,3-propanediamine (interm. 3-c).

EXAMPLE 2-c a) A mixture of (±)-3-[[(3,4-dihydro-2H-1-benzopyran-2-yl)methyl](phenylmethyl)amino]propanenitrile (0.069 mol) in methanol (250 ml) was hydrogenated with Raney nickel (5 g) as a catalyst. After uptake of hydrogen (2 eq.), the catalyst was filtered off and the filtrate was evaporated, yielding 20 g (94% crude residue) of (±)-N-[(3,4-dihydro-2H-1-benzopyran-2-yl)methyl]-N-(phenylmethyl)-1,3-propanediamine (interm. 4-c).

b) A mixture of intermediate (4-c) (0.01 mol) and 2-methylthio-4(1H)-pyrimidinone (0.01 mol) was heated for 2 hours at 150° C. The residue was purified by column chromatography over silica gel (eluent: $CH_2Cl_2/CH_3OH$ 95/5). The pure fractions were collected and the solvent was evaporated. The residue was converted into the hydrochloric acid salt (1:2) with HCl/2-propanol and crystallized from 1,1'-oxybisethane. The salt was filtered off and dried, yielding 2.8 g (56.5%) of (±)-2-[[3-[[(3,4-dihydro-2H-1-benzopyran-2-yl)methyl](phenylmethyl)amino]propyl]amino]-4(1H)-pyrimidinone dihydrochloride monohydrate; mp. 150.2° C. (interm. 5-c).

In a similar manner were prepared:

TABLE 1-c

[Structure: benzopyran-O-CH2-N(CH2-phenyl)-Alk-NH-Q]

| Int. No. | Alk | Q | Physical data |
|---|---|---|---|
| 5-c | —(CH₂)₃— | 4-hydroxy-2-pyrimidinyl | mp. 150.2° C./.2HCl.H₂O |
| 6-c | —(CH₂)₂— | 4-hydroxy-6-methyl-2-pyrimidinyl | mp. 212.1° C./.2HCl |
| 7-c | —(CH₂)₂— | 4-hydroxy-6-propyl-2-pyrimidinyl | mp. 190.5° C./.2HCl |
| 8-c | —(CH₂)₃— | 2-pyrazinyl | — |
| 9-c | —(CH₂)₃— | 5-chloro-2-pyridinyl | mp. 111.3° C./.2HCl.½H₂O |
| 10-c | —(CH₂)₃— | 2-chloro-4-pyrimidinyl | — |
| 11-c | —(CH₂)₃— | 2-methoxy-4-pyrimidinyl | — |
| 12-c | —(CH₂)₃— | 2-(dimetylamino)-4-pyrimidinyl | — |
| 13-c | —(CH₂)₃— | 2-(1-piperidinyl)-4-pyrimidinyl | — |
| 14-c | —(CH₂)₃— | 2-(methylamino)-4-pyrimidinyl | — |

EXAMPLE 3-c a) A mixture of 2-chlorocarbonyl-3,4-dihydro-2H-1-benzopyran (0.47 mol) in N,N-dimethylacetamide (100 ml), a solution of thiophene (4%) (3 ml) and 2,2'-oxybispropane (400 ml) was hydrogenated with palladium on activated carbon (10%) (5 g) as a catalyst. After uptake of hydrogen (1 eq.), the catalyst was filtered off and the filtrate was evaporated. The residue, potassium acetate (20 g) and benzenemethanamine (50 g) in N,N-dimethylacetamide (2 ml) and methanol (300 ml) was hydrogenated with palladium on activated carbon (10%) (5 g) as a catalyst. After uptake of hydrogen (1 eq.), the catalyst was filtered off and the filtrate was evaporated. The residue in methanol (500 ml) was hydrogenated with palladium on activated carbon (10%) (5 g) as a catalyst. After uptake of hydrogen (1 eq.), the catalyst was filtered off and the filtrate was evaporated. The residue was taken up in 1,1'-oxybisethane and washed with a NaOH-solution. The organic layer was dried (MgSO$_4$), filtered off and evaporated. The residue (70 g) was distilled at 70° C. (0.1 mm Hg), yielding 48.7 g (63.5%) of (±)-3,4-dihydro-2H-1-benzopyran-2-methanamine (interm. 15-c).

b) A mixture of intermediate (15-c) (0.12 mol) and 2-propenenitrile (0.12 mol) in ethanol (235 ml) was stirred and refluxed for 4 hours. The solvent was evaporated, yielding 27 g crude residue of (±)-3-[[(3, 4-dihydro-2H-1-benzopyran-2-yl)methyl]amino] propane-nitrile (interm. 16-c).

c) A mixture of intermediate (16-c) (0.12 mol) in methanol saturated with ammonia (500 ml) was hydrogenated with Raney nickel (6 g) as a catalyst. After uptake of hydrogen (2 eq.), the catalyst was filtered off and the filtrate was evaporated. The residue was purified by distillation, yielding 24 g (90.8%) of (±)-N-[(3,4-dihydro-2H-1-benzopyran-2-yl)methyl]-1,3-propanediamine (interm. 17-c).

B. Preparation of the final compounds (-c)

EXAMPLE 4-c

A mixture of intermediate (1-c) (0.058 mol), 3,4-dihydro-2H-1-benzopyran-2-carboxaldehyde (0.064 mol) and potassium acetate (7.1 g) in methanol (200 ml) was hydrogenated with platinum on activated carbon 5% (2 g) as a catalyst in the presence of a solution of thiophene (4%) (1 ml). After uptake of hydrogen (1 eq.), the catalyst was filtered off. The filtrate was evaporated. The residue was dissolved in H$_2$O/CH$_2$Cl$_2$ and alkalized with NaOH. The organic layer was separated, dried (MgSO$_4$), filtered and the solvent was evaporated. The residue was purified by column chromatography over silica gel (eluent: CH$_2$Cl$_2$/CH$_3$OH 90/10). Two fractions were collected. The first fraction was evaporated. The residue was crystallized from 2-propanol. The crystals were filtered off and dried. The second fraction was evaporated and the residue was crystallized from 2-propanol. The crystals were filtered off and dried, yielding 3.09 g (16%) of (±)-N-(6-chloro-3-pyridazinyl)-N'-[(3,4-dihydro-2H-1-benzopyran-2-yl)methyl]-1,3-propanediamine; mp. 107.8° C. (comp. 1-c).

EXAMPLE 5-c

Intermediate (5-c) (0.005 mol) was hydrogenated in methanol (250 ml) with palladium on activated carbon (2 g) as a catalyst. After uptake of hydrogen (1 eq.), the catalyst was filtered off. The solvent was evaporated. The residue (2 g) was recrystallized from methanol. The crystals were filtered off and dried, yielding 0.7 g (36%) of (±)-2-[[3-[[ (3,4-dihydro-2H-1-benzopyran-2-yl)methyl]amino]propyl] amino]-4(1H)-pyrimidinone dihydrochloride (comp. 8-c).

EXAMPLE 6-c

A mixture of intermediate (17-c) (0.03 mol) and 2-methylthio-4(1H)-pyrimidinone (0.03 mol) in 2-methoxyethanol (50 ml) was stirred and refluxed overnight. The solvent was evaporated. The residue was stirred in water and extracted with dichloromethane. The separated organic layer was dried (MgSO$_4$), filtered and the solvent was evaporated. The residue was purified by column chromatography over silica gel (eluent: CH$_2$Cl$_2$/(CH$_3$OH/NH$_3$) 95/5). The pure fractions were collected and the solvent was evaporated. This fraction was dissolved in 2-propanone and converted into the ethanedioic acid salt (2:3). The salt was filtered off and crystallized from methanol. The solid (1.2 g) was filtered off and dried, yielding 1.0 g (7.4%) of (±)-2-[[3-[[(3,4-dihydro-2H-1-benzopyran-2-yl)methyl]amino] propyl]amino]-4(3H)-pyrimidinone ethanedioate(2:3);

mp. 206.7° C. (comp. 9-c).

EXAMPLE 7-c

A mixture of (±)-N$^2$-[3-[[(3,4-dihydro-2H-1-benzopyran-2-yl)methyl]amino]propyl]-N$^4$,N$^4$-dimethyl-2,4-pyrimidinediamine dihydrochloride (0.0067 mol) in methanol (150 ml) was hydrogenated with palladium on activated carbon 10% (2 g) as a catalyst in the presence of a solution of hydrochloric acid in 2-propanol (2 ml). After uptake of hydrogen (2 eq.), the catalyst was filtered off. The filtrate was evaporated and the residue was crystallized twice from methanol. The crystals were filtered off and dried, yielding 0.32 g (13.1%) of (±)-2-[[3-[[(3,4-dihydro-2H-1-benzopyran-2-yl)methyl]amino]propyl]amino]-5,6-dihydro-4(3H)-pyrimidinone dihydrochloride; mp. 273.6° C. (comp. 12-c).

EXAMPLE 8-c

A mixture of compound (17-c) (0.02 mol) in methanol (200 ml) was hydrogenated with palladium on activated carbon 10% (2 g) as a catalyst. After uptake of hydrogen (2 eq.), the catalyst was filtered off. The filtrate was evaporated. The residue was dissolved in 2-propanol and converted into the hydrochloric acid salt (1:2) with HCl/2-propanol. The salt was filtered off and dried, yielding 5.61 g (75%) of (±)-N-[(3,4-dihydro-2H-1-benzopyran-2-yl)methyl]-N'-(3, 4,5,6-tetrahydro-2-pyridinyl)-1,3-propanediamine dihydrochloride; mp. 211.1° C. (comp. 15-c).

EXAMPLE 9-c

A mixture of the free base of compound (19-c) (0.0145 mol) and Raney nickel (5 g) in tetrahydrofuran (150 ml) was stirred and refluxed for 1 hour. The catalyst was filtered off and the filtrate was evaporated. The residue was dissolved in 2-propanone and converted into the ethanedioic acid salt (1:2). The salt was filtered off (3 g) and recrystallized from methanol (600 ml). The crystals were filtered off and dried, yielding 2.5 g (36.2%) of (±)-N-[(3,4-dihydro-2H-1-benzopyran-2-yl)methyl]-N'-4-pyrimidinyl-1,3-propanediamine ethanedioate(1:2); mp. 222.2° C. (comp. 20-c).

TABLE 2-c

Structure: R^A-substituted chroman-O-CH2-NH-(CH2)3-NH-pyridazine(N=N)-R^42

| Co. No. | Ex. No. | R^A | R^42 | Physical data |
|---|---|---|---|---|
| 1-c | 4-c | H | Cl | mp. 107.8° C. |
| 2-c | 4-c | H | H | mp. 169.7° C..2HCl.½H$_2$O |
| 3-c | 4-c | H | CH$_3$ | mp. 158.7° C./.2HCl.½H$_2$O |
| 4-c | 4-c | H | Cl | mp. 203.1° C./[α]$_D^{20}$ = −48.51° (c = 1% in methanol)/ (−)-(R).2HCl |
| 5-c | 4-c | 6-F | Cl | mp. 229.3° C./[α]$_D^{20}$ = −27.00° (c = 1% in methanol)/ (−)-(R).2HCl |
| 6-c | 4-c | 6-F | Cl | mp. 243.2° C./[α]$_D^{20}$ = +33.67° (c = 1% in methanol)/ (+)-(S).2HCl |
| 7-c | 6-c | 7-CH$_2$—CH$_3$ | Cl | mp. 223.9° C./.2HCl |
| 25-c | 4-c | 8-OCH$_3$ | Cl | mp. 182.6° C./.2HCl. H$_2$O |
| 26-c | 5-c | H | CN | mp. 192.3° C./(COOH)$_2$ |
| 27-c | 5-c | H | OH | mp. 191.1° C./(COOH)$_2$ |
| 28-c | 5-c | H | —C(=O)—NH$_2$ | mp. 211.7° C./(COOH)$_2$ |

TABLE 3-c

| Co. No. | Ex. No. | R^A | R^2 | R^1 | Alk | R^B | Physical data |
|---|---|---|---|---|---|---|---|
| 8-c | 5-c | H | H | H | —(CH$_2$)$_3$— | H | .2HCl |
| 9-c | 6-c | H | H | H | —(CH$_2$)$_3$— | H | mp. 206.7° C./.³⁄₂(COOH)$_2$ |
| 10-c | 6-c | H | H | H | —(CH$_2$)$_2$— | (CH$_2$)$_2$CH$_3$ | mp. 227.9° C./.2HCl |
| 11-c | 6-c | H | H | H | —(CH$_2$)$_2$— | H | mp. 227.6° C./.2HCl |

TABLE 4-c

| Co. No | Ex. No. | R^A | R^2 | R^1 | Physical data |
|---|---|---|---|---|---|
| 12-c | 7-c | H | H | H | mp. 273.6° C./.2HCl |

TABLE 5-c

| Co. No. | Ex. No. | R^A | R^2 | R^1 | Alk | R^B | Physical data |
|---|---|---|---|---|---|---|---|
| 13-c | 6-c | 6-F | H | H | —(CH$_2$)$_3$— | H | mp. 198.1° C./.2HCl |
| 14-c | 5-c | H | H | H | —(CH$_2$)$_3$— | H | mp. 188.9° C/.2HCl |

TABLE 6-c

| Co. No. | Ex. No. | R^A | R^2 | Alk | R^B | n | Physical data |
|---|---|---|---|---|---|---|---|
| 15-c | 8-c | H | H | —(CH$_2$)$_3$— | H | 2 | mp. 211.1° C./.2HCl |

Table 7-c

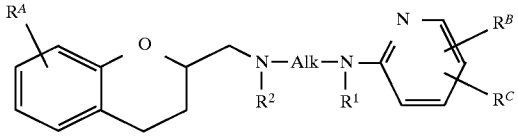

| Co. No. | Ex. No. | $R^A$ | $R^2$ | Alk | $R^1$ | $R^B$ | $R^C$ | Physical data |
|---|---|---|---|---|---|---|---|---|
| 16-c | 4-c | H | H | $-(CH_2)_3-$ | H | H | H | mp. 182.6° C./.2HCl |
| 17-c | 4-c | H | H | $-(CH_2)_3-$ | H | 6-$CH_3$ | 3-C(=O)$NH_2$ | mp. 246.9° C./.2HCl.$H_2O$ |

TABLE 8-c

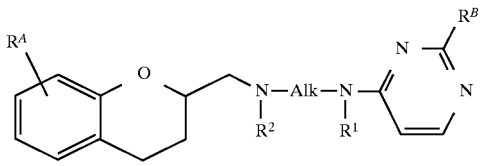

| Co. No. | Ex. No. | $R^A$ | $R^2$ | $R^1$ | Alk | $R^B$ | Physical data |
|---|---|---|---|---|---|---|---|
| 18-c | 6-c | H | H | H | $-(CH_2)_3-$ | $-S-CH_3$ | mp. 225.8°C./.2(COOH)$_2$ |
| 19-c | 10-c | H | H | H | $-(CH_2)_3-$ | H | mp. 222.2°C./.2(COOH)$_2$ |
| 20-c | 10-c | H | $CH_2CH_3$ | H | $-(CH_2)_3-$ | H | mp. 117.4°C./.2(COOH)$_2$.½$H_2O$ |
| 21-c | 5-c | H | H | H | $-(CH_2)_3-$ | $-O-CH_3$ | mp. 179.6°C./.2(COOH)$_2$ |
| 22-c | 5-c | H | H | H | $-(CH_2)_3-$ | $-N(CH_3)_2$ | mp. 204.6°C./.2(COOH)$_2$ |
| 23-c | 5-c | H | H | H | $-(CH_2)_3-$ | 1-piperidinyl | mp. 206.8°C./.2(COOH)$_2$ |
| 24-c | 5-c | H | H | H | $-(CH_2)_3-$ | $-NH-CH_3$ | mp. 188.1°C./.2(COOH)$_2$ |

TABLE 9-c

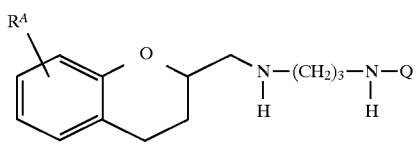

| Co. No. | Ex. No. | $R^A$ | Q | Physical data |
|---|---|---|---|---|
| 29-c | 6-c | 6-F | 2-thiazolyl | mp. 145.3° C./.2 HCl |
| 30-c | 5-c | H | 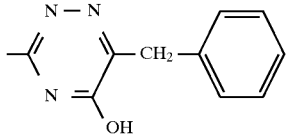 | mp. 156.2° C. |
| 31-c | 5-c | R | 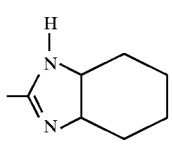 | mp. 214.1° C. |

TABLE 9-c-continued

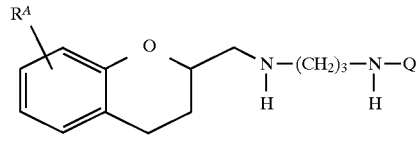

| Co. No. | Ex. No. | $R^A$ | Q | Physical data |
|---|---|---|---|---|
| 32-c | 5-c | H | 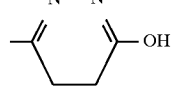 | mp. 184.9° C./(COOH)$_2$ |
| 33-c | 6-c | H | 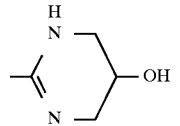 | mp. 168.2° C. |

TABLE 10-c

[Structure: chroman-2-yl-CH2-N(H)-(CH2)3-N(R1)-C(=N-R^A)-N(R^C)-R^B]

| Co. No. | Ex. No. | $R^1$ | $R^A$ | $R^B$ | $R^C$ | Physical data (mp in °C.)/base/salt |
|---|---|---|---|---|---|---|
| 34-c | 6-c | H | CN | 2-phenylethyl | methyl | 159.4/.2(COOH)$_2$ |
| 35-c | 9-c | H | H | 2-phenylethyl | methyl | 198.5 |
| 36-c | 6-c | H | CN | (2-methoxyphenyl)methyl | methyl | 166.1/(COOH)$_2$ |
| 37-c | 9-c | H | H | (2-methoxyphenyl)methyl | methyl | 191.9/2HCl |
| 38-c | 6-c | H | CN | 4-methyl-1-piperazinyl | | 171.6 |
| 39-c | 6-c | CH$_3$ | CN | phenylmethyl | methyl | 142.9/(COOH)$_2$ |
| 40-c | 9-c | H | H | cyclohexyl | H | 242.5/2HCl |
| 41-c | 9-c | H | C(=O)NH$_2$ | cyclohexyl | H | 201.5/2HCl |

D. Pharmacological Example

EXAMPLE 1-d

Segments of basilar arteries taken from pigs (anaesthetised with sodium pentobarbital) were mounted for recording of isometric tension in organ baths. The preparations were bathed in Krebs-Henseleit solution. The solution was kept at 37° C. and gassed with a mixture of 95% O$_2$–5% CO$_2$. The preparations were stretched until a stable basal tension of 2 grams was obtained.

The preparations were made to constrict with serotonin ($3 \times 10^{-7}$M). The response to the addition of serotonin was measured and subsequently the serotonin was washed away. This procedure was repeated until stable responses were obtained. Subsequently the test compound was administered to the organ bath and the constriction of the preparation was measured. This constrictive response was expressed as a percentage of the response to serotonin as measured previously. The lowest active concentration was defined as the concentration at which 50% of the response to serotonin is obtained.

In table 3 the lowest active concentration of compounds of formula (I) are presented.

TABLE 1-d

| Co. No. | Lowest active concentration (M) |
|---|---|
| 1-a | $3 \cdot 10^{-8}$ |
| 2-a | $3 \cdot 10^{-7}$ |
| 4-a | $1 \cdot 10^{-6}$ |
| 5-a | $3 \cdot 10^{-7}$ |
| 9-a | $1 \cdot 10^{-8}$ |
| 10-a | $3 \cdot 10^{-9}$ |
| 11-a | $3 \cdot 10^{-8}$ |
| 12-a | $3 \cdot 10^{-8}$ |
| 13-a | $3 \cdot 10^{-7}$ |

TABLE 2-d

| Co. No. | Lowest active concentration (M) |
|---|---|
| 1-b | $1 \cdot 10^{-7}$ |
| 3-b | $3 \cdot 10^{-7}$ |
| 4-b | $3 \cdot 10^{-8}$ |
| 5-b | $3 \cdot 10^{-8}$ |
| 6-b | $1 \cdot 10^{-7}$ |
| 7-b | $3 \cdot 10^{-9}$ |

TABLE 3-d

| Co. no. | Lowest active concentration (M) |
|---|---|
| 1-c | $1 \cdot 10^{-6}$ |
| 3-c | $1 \cdot 10^{-7}$ |
| 4-c | $1 \cdot 10^{-7}$ |
| 5-c | $3 \cdot 10^{-7}$ |
| 12-c | $1 \cdot 10^{-6}$ |
| 13-c | $<3 \cdot 10^{-7}$ |
| 14-c | $1 \cdot 10^{-7}$ |
| 15-c | $3 \cdot 10^{-8}$ |
| 16-c | $1 \cdot 10^{-6}$ |
| 18-c | $1 \cdot 10^{-7}$ |
| 19-c | $3 \cdot 10^{-7}$ |
| 21-c | $1 \cdot 10^{-7}$ |
| 22-c | $1 \cdot 10^{-6}$ |
| 23-c | $3 \cdot 10^{-7}$ |
| 24-c | $3 \cdot 10^{-8}$ |

E. Composition examples

"Active ingredient" (A.I.) as used throughout these examples relates to a compound of formula (I), a pharmaceutically acceptable acid addition salt or a stereochemically isomeric form thereof.

EXAMPLE 1-e

ORAL DROPS

500 Grams of the A.I. was dissolved in 0.5 l of 2-hydroxypropanoic acid and 1.5 l of the polyethylene glycol at 60°–80° C. After cooling to 3°~40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 2-e

ORAL SOLUTION

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 3-e
CAPSULES
20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE 4-e
FILM-COATED TABLETS
Preparation of tablet core
A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.
Coating
To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE 5-e
INJECTABLE SOLUTION
1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

EXAMPLE 6-e
SUPPOSITORIES
3 Grams A.I. was dissolved in a solution of 3 grams 2,3-eihydroxybutanedioic acid in 25 ml polyethylene glycol 400. 12 Grams surfactant (SPAN®) and triglycerides (Witepsol 555 ®) q.s. ad 300 grams were molten together. The latter mixture was mixed well with the former solution. The thus obtained mixture was poured into moulds at a temperature of 37°–38° C. to form 100 suppositories each containing 30 mg/ml of the A.I.

EXAMPLE 7-e
INJECTABLE SOLUTION
60 Grams of A.I. and 12 grams of benzylalcohol were mixed well and sesame oil was added q.s. ad 1 l, giving a solution comprising 60 mg/ml of A.I. The solution was sterilized and filled in sterile containers.

We claim:
1. A compound having the formula:

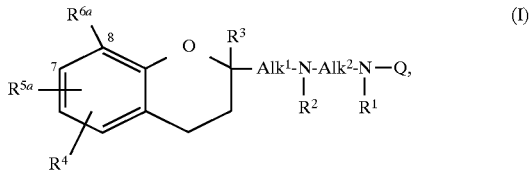

a pharmaceutically acceptable acid or base addition salt thereof, or a stereochemically isomeric form thereof, wherein $R^1$, $R^2$ and $R^3$ each independently are hydrogen or $C_{1-6}$alkyl;

$R^4$ is hydrogen, halo, $C_{1-6}$alkyl, hydroxy, $C_{1-6}$alkyloxy, aryloxy or arylmethoxy;

$R^{5a}$ and $R^{6a}$ are taken together to form a bivalent radical, which is linked to the 7 and 8 position of the dihydrobenzopyran moiety, and has the formula

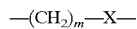

or

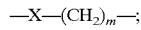

in these bivalent radicals one or two hydrogen atoms may be substituted with $C_{1-6}$alkyl, $C_{1-6}$alkylcarbonyl or $C_{1-6}$alkyl-$S(O)$—;

X is —O—, —S—, —S(O)—, —S(O)$_2$—, —C(O)— or —NR$^7$—;

m is 2 or 3;

$R^7$ is hydrogen, $C_{1-6}$alkyl, $C_{1-6}$alkylcarbonyl or $C_{1-6}$alkyl-$S(O)$—;

Alk$^1$ is $C_{1-5}$alkanediyl;

Alk$^2$ is $C_{2-15}$alkanediyl; and

Q is a radical of formula

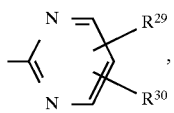

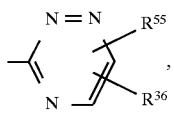

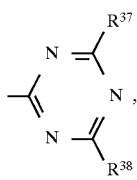

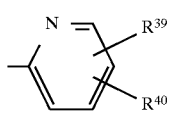

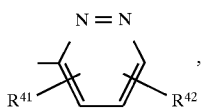

-continued

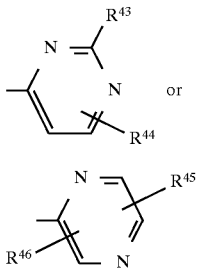

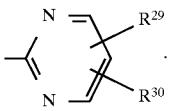

wherein $R^{29}$, $R^{30}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$ and $R^{55}$ each independently are hydrogen, hydroxy, halo, $C_{1-6}$alkyl, $C_{1-6}$alkyloxy, aryloxy, aryl$C_{1-6}$alkyl, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl or pyrrolidinyl.

2. The compound of claim 1 wherein Q is a radical of the formula

3. The compound of claim 1, selected from:
N-[(2,3,4,7,8,9-hexahydrobenzo[2,1-b:3,4-b']-dipyran-2-yl)methyl]-N'-2-pyrimidinyl-1,3-propanediamine;
(±)-N-[(2,3,4,8,9,10-hexahydrobenzo[2,1-b:3,4-b']-dipyran-2-yl)methyl]-N'-2-pyrimidinyl-1,3-propanediamine; or
N-2-pyrimidinyl-N'-[(3,6,7,8-tetrahydro-2,3-dimethyl-2H-furo[3,2-h][1]benzopyran-8-yl)methyl]-1,3-propanediamine; or a pharmaceutically acceptable acid addition salt, or stereochemically isomeric form thereof.

4. A composition comprising a pharmaceutically acceptable carrier and as an active ingredient a therapeutically effective amount of a compound as claimed in claim 1.

5. A method for inducing vasoconstriction which comprises administering to a patient in need of the same an effective amount of a compound as defined in claim 1.

6. A method for inducing vasoconstriction which comprises administering to a patient in need of the same an effective amount of a compound as defined in claim 2.

7. A method for inducing vasoconstriction which comprises administering to a patient in need of the same an effective amount of a compound as defined in claim 3.

* * * * *